(12) United States Patent
Markle et al.

(10) Patent No.: US 9,075,013 B2
(45) Date of Patent: Jul. 7, 2015

(54) APPARATUS AND METHODS FOR MICROSCOPY HAVING RESOLUTION BEYOND THE ABBE LIMIT

(71) Applicant: Periodic Structures, Inc., Los Gatos, CA (US)

(72) Inventors: David A. Markle, Saratoga, CA (US); Hwan J. Jeong, Los Altos, CA (US); John S. Petersen, Austin, TX (US)

(73) Assignee: Periodic Structures, Inc., Los Gatos, CA (US)

( * ) Notice: Subject to any disclaimer, the term of this patent is extended or adjusted under 35 U.S.C. 154(b) by 294 days.

(21) Appl. No.: 13/871,034

(22) Filed: Apr. 26, 2013

(65) Prior Publication Data

US 2013/0286179 A1    Oct. 31, 2013

Related U.S. Application Data

(60) Provisional application No. 61/639,947, filed on Apr. 29, 2012.

(51) Int. Cl.
*H04N 7/18* (2006.01)
*G01N 21/64* (2006.01)

(52) U.S. Cl.
CPC .................................. *G01N 21/6458* (2013.01)

(58) Field of Classification Search
CPC ............. G02B 21/365; G02B 21/0072; G02B 21/0076; G01N 21/6447; G01N 21/6458; B82Y 10/00
See application file for complete search history.

(56) References Cited

U.S. PATENT DOCUMENTS

| | | | | |
|---|---|---|---|---|
| 5,304,613 A * | 4/1994 | Oka | ............................... | 525/540 |
| 5,731,588 A * | 3/1998 | Hell et al. | .................. | 250/458.1 |
| 5,777,342 A * | 7/1998 | Baer | .......................... | 250/492.2 |
| 5,866,911 A * | 2/1999 | Baer | .......................... | 250/458.1 |
| 6,903,347 B2 * | 6/2005 | Baer | .......................... | 250/492.2 |
| 7,071,477 B2 * | 7/2006 | Baer | .......................... | 250/492.2 |
| 7,642,536 B2 * | 1/2010 | Baer | ............................. | 250/584 |
| 8,311,788 B2 * | 11/2012 | Hurley et al. | ...................... | 703/9 |
| 8,547,533 B2 * | 10/2013 | Knutson et al. | .................. | 356/16 |
| 8,725,477 B2 * | 5/2014 | Zhang et al. | ...................... | 703/10 |
| 2009/0237501 A1 * | 9/2009 | Lemmer et al. | .................. | 348/79 |
| 2009/0263002 A1 * | 10/2009 | Cremer et al. | ................ | 382/133 |
| 2013/0093871 A1 * | 4/2013 | Nowatzyk et al. | .............. | 348/79 |

* cited by examiner

*Primary Examiner* — Victor Kostak
(74) *Attorney, Agent, or Firm* — Opticus IP Law PLLC

(57) ABSTRACT

Microscope apparatus and methods for imaging an object with a resolution beyond the Abbe limit are disclosed. The apparatus employs an object selectively patterned with a fluorescing material that is induced to fluoresce with one wavelength and inhibited from fluorescing with a second wavelength. Two orthogonal interference-fringe patterns are generated from four diffracted light beams of an inhibiting wavelength and superimposed on the object along with light that induces fluorescence. The interference-pattern image allows only sub-resolution-sized emission areas of the object to fluoresce. Multiple images of the fluorescing object are obtained, each corresponding to a slightly different position of the fringe patterns on the substrate. Each image is processed to yield a sparsely sampled super-resolution image. Multiple sparse images are interwoven to form a complete super-resolution image of the object.

20 Claims, 18 Drawing Sheets

APPARATUS AND METHODS FOR MICROSCOPY HAVING RESOLUTION BEYOND THE ABBE LIMIT

CLAIM OF PRIORITY & CROSS-REFERENCE TO RELATED APPLICATIONS

This Application claims priority under 35 U.S.C. §119(e) from U.S. Provisional Application Ser. No. 61/639,947, filed on Apr. 29, 2013, which Application is incorporated by reference herein.

This Application is related to U.S. patent application Ser. No. 13/678,692, filed on Nov. 16, 2012, and which is incorporated by reference herein.

FIELD

The present disclosure relates to microscopy, and in particular microscopy apparatus and methods that have a resolution beyond the Abbe limit.

BACKGROUND ART

Microscopes, like all image-forming optical instruments, have limited resolving ability ("resolution") even if the optical components are made perfectly. The limited resolution is due to diffraction that occurs at the aperture stop or pupil of the instrument. This fundamental phenomenon was first explained in 1873, by Ernst Karl Abbe. Abbe explained that the smallest possible image that can be formed by a microscope objective has a spot radius r given by: $r = (\lambda/2) \cdot n \cdot \sin(\theta)$, where r is the radius of the smallest possible spot, $\lambda$ is the wavelength of the light used to form the image, n is the index of refraction of the medium containing the image and $\theta$ is the angle between the axis and the outermost ray forming the image in the medium containing the image.

The quantity $n \cdot \sin(\theta)$ is known as the numerical aperture (NA). Thus, the above equation can be rewritten as: $r = \lambda/(2 \cdot NA)$.

If two points of equal intensity are observed through a microscope objective, then the minimum separation s that can be resolved is given by Abbe's formula: $s = 0.61 \lambda/NA$. This is also called the "Abbe limit."

According to the Abbe formula, the resolving power of a microscope objective can be improved via the use of shorter wavelengths and/or a higher NA. However, the maximum value of the NA is limited by the index of refraction of available immersion liquids (oil and water being generally preferred) and the maximum value of the sine function, which is unity. In practice, the maximum value of NA is about 1.35. The shortest wavelength visible to the eye is about 0.43 microns, and for lithography the shortest wavelength currently in general use is a deep-UV, excimer-laser wavelength of 193 nm.

Using very complicated mask patterns and manipulating the angle and polarization of the incident light, as well as the relative phase of the light transmitted through the mask pattern, makes it possible to improve the resolution limit achieved in a lithography system beyond that predicted by Abbe by about a factor of less than 2. This is achieved only with great difficulty and under very special conditions. Diffraction is a fundamental part of image formation and cannot be avoided.

SUMMARY

This disclosure is directed to a microscope and microscope methods having a resolution limit beyond the Abbe limit. The apparatus and methods involve capturing images of an object supported by a substrate. The object comprises a material that is stimulated to fluoresce with a first wavelength and inhibited from fluorescing with a second wavelength. The resolution of the microscope is mainly determined by an interference-pattern image that in an example is formed by two orthogonally oriented interference fringe patterns. The interference-pattern image is formed using a wavelength of light that inhibits fluorescence. Another wavelength of light illuminates the object and activates the fluorescence. Consequently, the object fluoresces from only small regions between the fringes of the interference-pattern image where the inhibition intensity is substantially zero. The higher the ratio of the inhibiting intensity to the stimulation intensity, the smaller the fluorescing areas (emission areas) of the object, and the higher the potential resolution.

For convenience the activation light is referred to herein as "blue," although it could be any wavelength, and the fluorescent light is referred to herein as "red," although it could be any wavelength longer than the activation wavelength. For example, the activation wavelength referred to as "blue" could be generated by a laser diode operating at 405 nm in the deep blue part of the spectrum, and the fluorescence spectrum referred to as "red" could extend from 480 nm to 600 nm, which includes green, yellow, orange and red components. The inhibition wavelength, from which the interference patterns are formed, is referred to herein as "green," although it could be any wavelength contained in the fluorescence spectrum and is preferably one on the long wavelength side of the peak of the emission spectrum.

The fluorescent light emitted by the object is imaged onto a photodetector that has an array of detector elements (i.e., a photodetector array). The photodetector converts the captured image into an electronic image. The images of adjacent fluorescent areas on the object overlap at the photodetector. A de-convolution algorithm is used to separate the images of the fluorescent areas.

By incrementally moving the fringe patterns in the interference-pattern image and capturing images corresponding to each fringe position, a composite picture of the object having a substantial increase in resolution is obtained.

The microscope apparatus and methods disclosed herein are expected to find widespread application in the inspection of masks and wafers used in the manufacture of semiconductors, as well as in biology where in vivo inspection using visible wavelengths is preferred.

An aspect of the disclosure is a method according to which a super-resolution image of an object that fluoresces at an activation wavelength is formed and is inhibited from fluorescing at an inhibition wavelength. The method includes: a) using light having the inhibition wavelength, sequentially forming $n^2$ interference-pattern images on the object to define fluorescence emission areas of the object, where n is an integer equal to 2 or greater; b) illuminating the object with light of the activation wavelength for each of the $n^2$ interference-pattern images to cause the fluorescence emission areas to emit fluorescent light at a fluorescent wavelength; c) capturing $n^2$ sparse object images that include images of the emission areas convolved with respective point spread functions (PSF), wherein the emission areas are smaller than the PSFs; d) for each of the sparse object images, de-convolving each of the emission-area images to obtain emission-area image intensities; and e) combining the emission-area image intensities from the $n^2$ sparse object images to form the super-resolution image of the object.

Another aspect of the disclosure is the method as described above and further comprising determining positions of the emission areas by capturing an image of one of the interference-pattern images and performing a Fourier analysis of the captured interference-pattern image.

Another aspect of the disclosure is the method as described above and further including displaying the super-resolution image in a manner representative of the emission-area intensities.

Another aspect of the disclosure is the method as described above, wherein the PSFs are determined as a function of the position at the object (i.e., as a function of the field at the object).

Another aspect of the disclosure is the method as described above and further comprising performing a calibration that comprises at least one of: i) measuring and compensating for a distortion in the interference-pattern image; and ii) measuring and compensating for a non-uniformity of the activation wavelength illumination.

Another aspect of the disclosure is the method as described above, wherein the object comprises a photoresist layer.

Another aspect of the disclosure is the method as described above, wherein the interference-pattern image is formed by at least two pairs of diffracted light beams.

Another aspect of the disclosure is the method as described above, wherein the $n^2$ interference-pattern images consist of crossed interference fringes, and where forming the different interference-pattern images includes shifting the interference fringes.

Another aspect of the disclosure is the method as described above, wherein the captured $n^2$ sparse object images are stored in a computer-readable memory, and wherein instructions embodied in a computer-readable medium cause a computer to perform acts d) and e).

Another aspect of the disclosure is the method as described above, wherein the light of the activating wavelength has a first intensity, the light of the inhibiting wavelength has a second intensity, and wherein the first and second intensities are selected to define a select size for the fluorescence emission areas.

Another aspect of the disclosure is the method as described above, further including scanning the object relative to an objective lens and a photodetector while maintaining the sparse object images at a substantially fixed position at the photodetector.

Another aspect of the disclosure is the method as described above, further including capturing with the photodetector at least one of: i) an image of the interference-pattern image, and ii) the activation-light illumination.

Another aspect of the disclosure is the method as described above, further comprising capturing an image of the object at the first wavelength and inspecting the captured image to evaluate a characteristic of at least one of: i) one or more of the interference-pattern images and ii) the activation-light illumination.

Another aspect of the disclosure is the method as described above, wherein each sparse object image is captured by a photodetector comprising an array of detector elements, each having a detector-element size, and further comprising reducing or eliminating a quantization effect caused by the array of detector elements by quantizing the PSFs to substantially match the detector-element size.

Another aspect of the disclosure is the method as described above, further including performing calibration imaging using a calibration artifact in place of the object.

Another aspect of the disclosure is a microscope for forming a super-resolution image of an object that fluoresces at an activation wavelength and is inhibited from fluorescing at an inhibition wavelength. The microscope includes an objective lens arranged adjacent the object, the objective lens having a resolution and at least one PSF; an interference pattern generator that operates cooperatively with the objective lens to generate an interference-pattern image on the object with first light of the inhibition wavelength; a light-source system that operates cooperatively with the objective lens to illuminate the object with second light having the activation wavelength, thereby defining on the object, in combination with the interference-pattern image, a plurality of sub-resolution fluorescence emission areas that emit fluorescent light; a fluorescence camera and filter that operate cooperatively with the objective lens to capture an image of the fluorescence emission areas and in response generate a photodetector signal; and a controller that receives the photodetector signal, the controller having instructions embodied in a computer-readable medium that cause the controller to perform a de-convolution of the captured image based on the at least one PSF to determine emission-area image intensities that define the super-resolution image.

Another aspect of the disclosure is the microscope as described above, wherein the interference-pattern image comprises at least first and second sets of interference fringes, and wherein the image-pattern generator is adapted to shift at least one of the first and second sets of interference fringes relative to the object to shift a location of the fluorescence emission areas.

Another aspect of the disclosure is the microscope as described above, wherein the photodetector includes an array of detector elements and wherein the captured image includes image pixels defined by the images of the fluorescence emission areas, with each pixel covered by at least two detector elements.

Another aspect of the disclosure is the microscope as described above, wherein the object is supported by a stage that is moveable relative to the objective lens.

Another aspect of the disclosure is the microscope as described above, wherein the interference-pattern generator and light-source system are adapted to control respective first and second intensities of the first and second light, wherein the first and second intensities define a size of the fluorescence emission areas.

Another aspect of the disclosure is the microscope as described above, further including an inspection camera that operates cooperatively with the objective lens to capture images of the object at the first wavelength.

Another aspect of the disclosure is the microscope as described above, further including means for synchronizing movement of the interference-pattern image with movement of the object.

DETAILED DESCRIPTION

The claims as set forth below are incorporated into and constitute part of this Detailed Description.

The terms "snapshot," "captured image," "exposure," "frame," "image," "image frame," and "picture" are used synonymously herein.

The terms "emission area," "fluorescence emission area," and "super-resolution element" are used synonymously herein.

The term "image pixel" refers to the image of an emission area.

The term "detector element" refers to a imaging element in a digital detector or image sensor. These detector elements are also called "pixels," but this term is reserved for use in the term "image pixel" as noted immediately above.

In the description below and in the claims, the parameter n is an integer equal to 2 or greater, and an imaging resolution improved by a factor of n requires $n^2$ snapshots. The parameter n is also the ratio of the fringe-pattern spacing to the width of a super-resolution element.

It is noted that n is also used to represent the refractive index, and one skilled in the art will understand by the particular context how n is being used in its various capacities.

Figure 1:
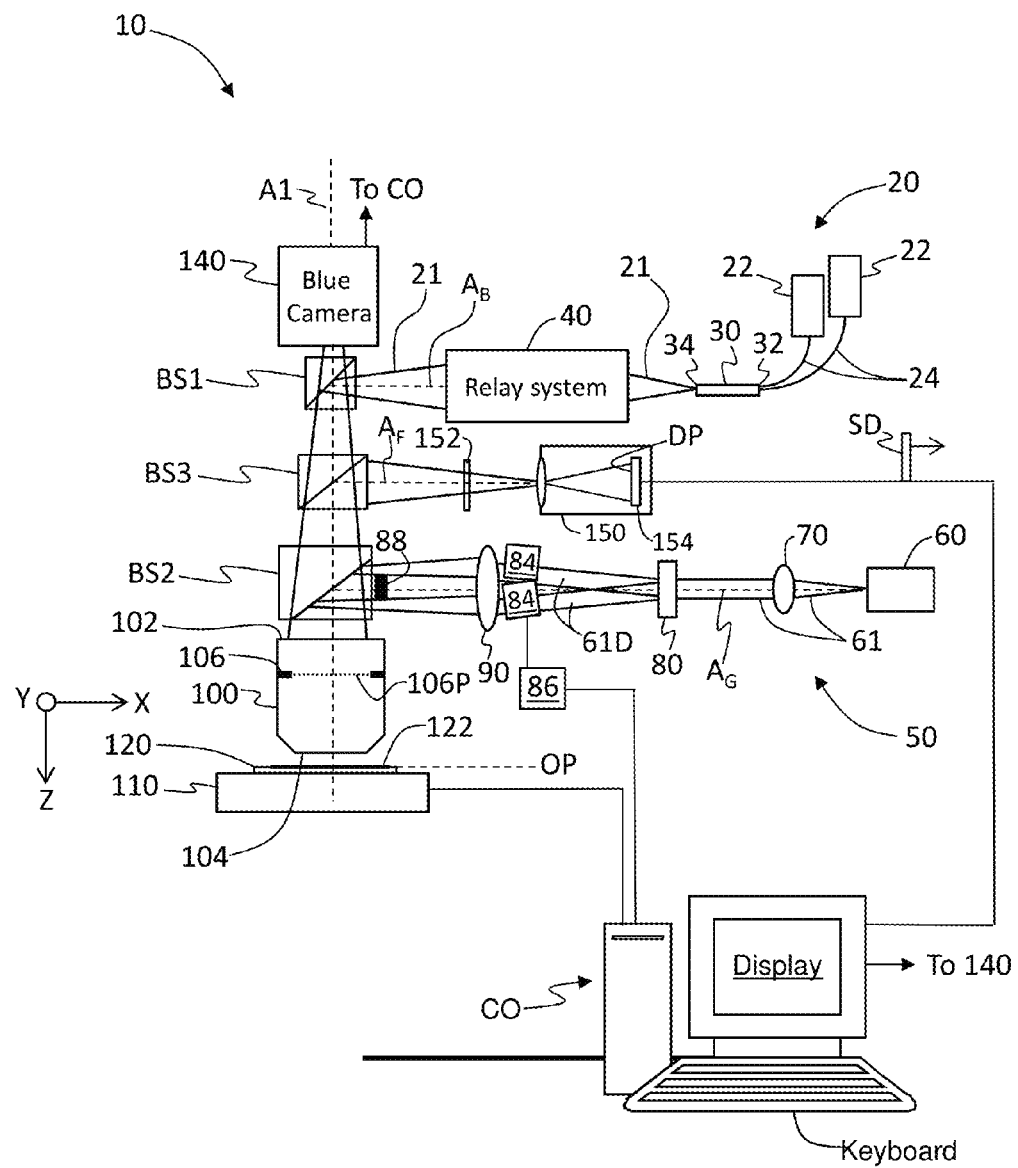
FIG. 1 is a schematic diagram of an example microscope according to the disclosure.

FIG. 1 is a schematic diagram of an example embodiment of a microscope apparatus ("microscope") 10 according to the disclosure. The microscope 10 includes an activating "blue" light-source system 20 that includes one or more light emitters 22, such as laser diodes, that emit light 21 of a first wavelength $\lambda_1$. The light 21 is activation light and first wavelength $\lambda_1$ is an activation wavelength, as explained in greater detail below.

In an example, light emitters 22 are each optically coupled to a light homogenizer 30 that includes an input end 32 and an output end 34. The optical coupling may be accomplished by respective optical fibers 24 that each lead from one of the blue light sources 22 to the input end 32 of light homogenizer 30. The blue light 21 passes through light homogenizer 30, and the light homogenizer homogenizes (uniformizes) this light, which is then outputted at output end 34. The outputted blue light 21 is then relayed by a relay system 40 along a blue optical axis AB to a first beam splitter BS1 that is arranged along a main axis A1.

The microscope 10 also includes an interference pattern generator (IPG) 50. The IPG 50 includes an inhibition "green" light source 60 that generates "green" light 61 along a green axis $A_G$. The green light 61 is inhibition light and has a green (second) inhibition wavelength $\lambda_2$ as discussed below. In an example, green light source 60 includes a laser. The IPG 50 also includes a lens 70 and a phase grating 80 each arranged along green axis $A_G$. The IPG 50 also includes phase shifters 84. The lens 70 is configured to collimate green light 61 to form a green light beam, which is made incident upon phase grating 80. This generates ±1st order green diffraction beams 61D of substantially equal intensity, each of which enters one of the corresponding phase shifters 84.

Figure 2:
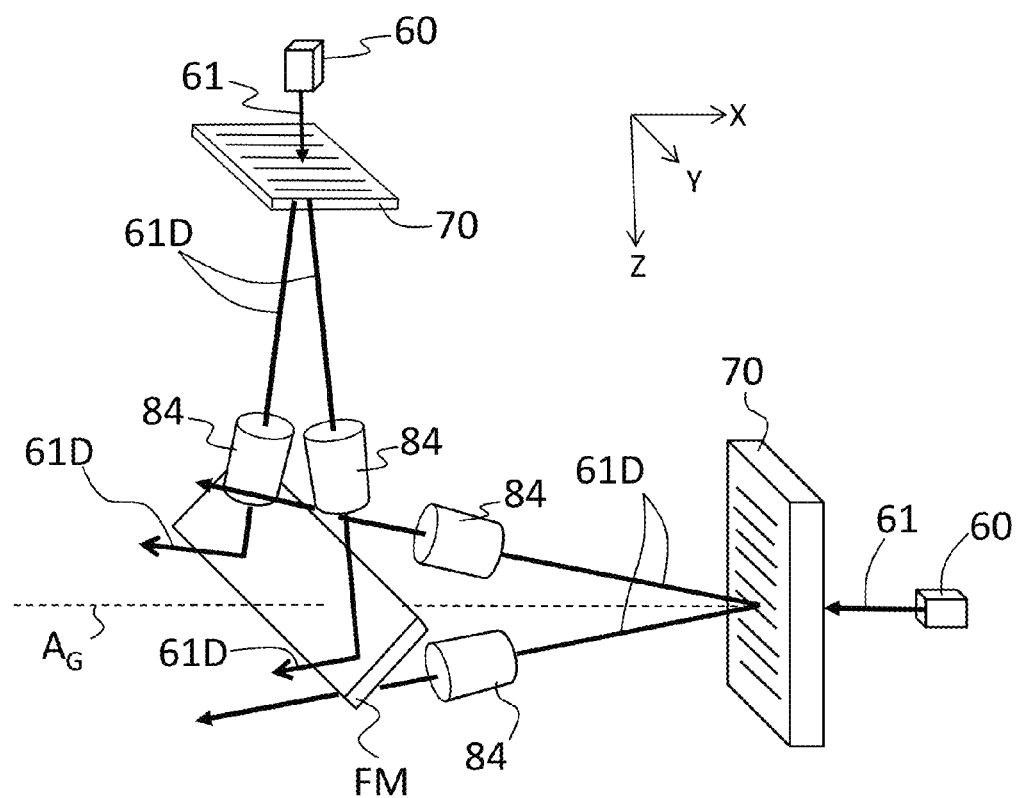
FIG. 2 is a close-up view of a portion of the interference pattern generator that shows four diffracted light beams and four phase-shifters.

Only two phase shifters 84 are shown in FIG. 1. In practice, there are two more phase shifters 84 that reside in the orthogonal direction, as illustrated in the close-up view of FIG. 2. Thus, a second set of green diffraction beams 61D are folded to travel along green axis $A_G$ using a fold mirror FM that resides along the green axis. The pairs of green diffraction beams 61D are focused by a focusing lens 90 and directed to a second beam splitter BS2 arranged along axis A1. The second beam splitter BS2 is dichroic and thus substantially reflects green light 61 while substantially passing blue light 21.

The maximum phase shift required in either set of diffraction beams 61D is 360°, which, in theory, can be done with a single phase-shifter 84. However, less phase shift is required from each phase shifter 84 if two phase shifters are used. This also helps to keep the intensities of the two diffraction beams 61D in each pair of diffracted beams equal. Example phase shifters 84 include Pockels cells, Kerr cells and an arrangement containing an acousto-optic modulator.

The microscope 10 also includes an objective lens 100 arranged along main axis A1. The objective lens 100 has an input end 102 and an output end 104. The input end 102 of objective lens 100 resides adjacent second beam splitter BS2 while the output end 104 resides adjacent a substrate stage 110 that supports a substrate 120 at an object plane OP of objective lens 100. The objective lens 100 also includes a pupil 106 that defines a pupil plane 106P. The objective lens 100 is color-corrected and is also telecentric.

Figure 3A:
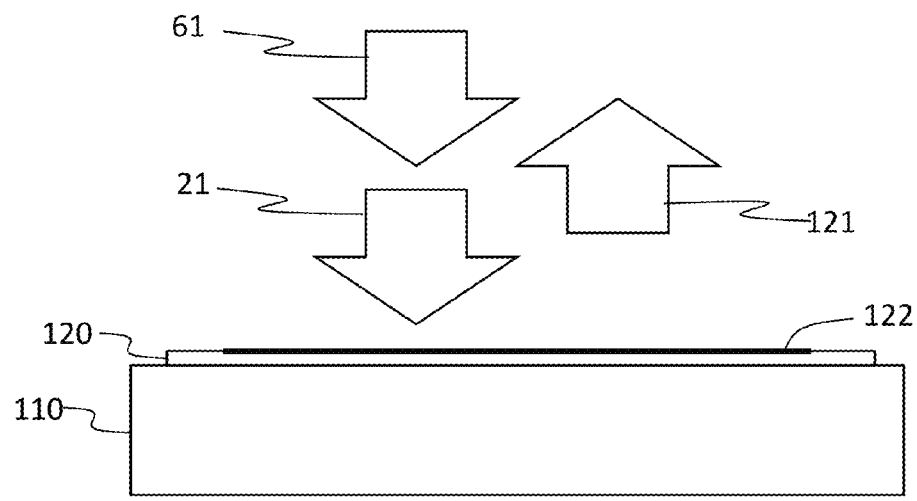
FIG. 3A is a schematic diagram of the object supported by the substrate and showing the activation ("blue") light, the inhibition ("green") light incident upon the object, and the fluorescent ("red") light emitted by those areas of the substrate not inhibited by the interference-pattern image formed by the inhibition light.

FIG. 3A is a close-up side view of substrate stage 110 and substrate 120. The substrate 120 supports an object 122 to be imaged. In an example, object 122 comprises a two-color fluorescent material that is activated with activation wavelength $\lambda_1$, causing it to fluoresce "red" light 121 over a broad spectrum. The object 122 is inhibited from fluorescing by exposure to green light 61, which has the aforementioned inhibition wavelength $\lambda_2$.

A lithography system for creating small features in a two-color photoresist is described in the following three U.S. Provisional Patent Applications, which are incorporated by reference herein: 61/561,545; 61/597,855; and 61/613,742. For the lithography application, absorption of the exposure light leads to an irreversible exposed condition unless the process is interrupted by the inhibiting light prior to entering the exposed condition. For the present microscopy application, there is no need for such an exposed condition. All that is necessary is that fluorescence be able to be induced with one wavelength and inhibited with another wavelength. Both of these properties may be possible with the same material.

The two-color lithography resist (after development) can also serve as a fluorescent material that fluoresces when exposed to one wavelength and is inhibited when exposed to a second wavelength. Such a resist system can be employed in a microscope that operates in a similar fashion to the exposure tool and thereby achieves imagery with a resolution that exceeds the Abbe diffraction limit associated with conventional optical microscopes.

In another example, object 122 may comprise special compounds added to the photoresist surface or contained in the resist layer, or it may be a resist layer having natural fluorescence, so it fluoresces when it is exposed to one wavelength (blue) and is inhibited from fluorescing when exposed to another wavelength (green). Thus the apparatus and methods described herein can be used to image either masks or wafers coated with a two-color resist that have been patterned, or, for that matter, any object containing a substance that can be induced to fluoresce with one wavelength and inhibited from fluorescing with another wavelength. The microscope 10 may also find application in other fields such as biology, where two-color materials are attached to certain organs or molecules or like biological material to more clearly differentiate the material from its surrounds.

With reference again to FIG. 1, microscope 10 optionally includes a blue camera 140 arranged along main axis A1 adjacent first beam splitter BS1. The blue camera 140 can be used to inspect object 122 using blue light 21 reflected or scattered by the object. Thus, blue camera 140 can also be referred to as inspection camera 140. The resolution obtained by blue camera 140 is limited by diffraction as predicted by Abbe. The image obtained with the blue camera 140 can be useful for alignment and for correcting the super-resolution image for illumination non-uniformities and for non-uniformities induced by the interference effects in object 122.

Figure 4:
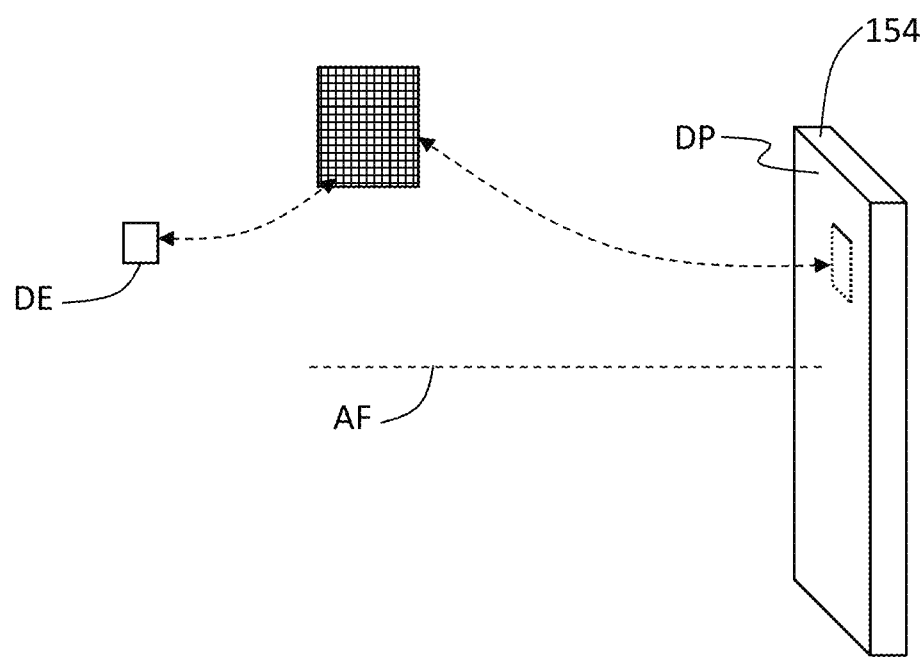
FIG. 4 is a close-up view of an example photodetector of the fluorescence camera, showing an example photodetector comprising an array of detector elements.

The microscope 10 also includes a fluorescence camera 150 arranged along an axis $A_F$ that intersects the main axis A1 at a third beam splitter BS3 that resides between first and second beam splitters BS1 and BS2. A filter 152 resides along axis $A_F$ between third beam splitter BS3 and fluorescence camera 150 and is configured to pass fluorescent (red) light 121 from object 122 while substantially blocking other wavelengths, in particular the blue and narrow-band green (inhibition) wavelengths $\lambda_1$ and $\lambda_2$. The third beam splitter BS3 is configured to deflect fluorescent light 121 from object 122 to the fluorescence camera 150. The fluorescence camera 150 includes a photodetector (i.e., image sensor) 154 operably disposed at a detector plane DP of the camera. FIG. 4 is a close-up view of photodetector 154 showing an example of the photodetector comprising an array of detector elements DE. The photodetector 154 generates a detector signal SD in response to receiving fluorescent light 121 from object 122 as discussed below.

The microscope 10 also includes a controller CO. The controller CO is operably connected to all the electrically controlled devices and components in microscope 10. The controller CO includes a display and a keyboard that serve as an operator interface. In an example, the display is used to display the super-resolution image in a manner representative of the emission-area intensities that make up the super-resolution image, as described below.

In one embodiment, controller CO includes a device, for example, a floppy disk drive, CD-ROM drive, DVD drive, magnetic optical disk (MOD) device (not shown) or any other digital device including a network connecting device such as an Ethernet device or an optical fiber-based network (not shown) for reading instructions and/or data from a computer-readable medium, such as a CD-ROM, a DVD, a MOD or any other digital source such as a network or the Internet, as well as yet-to-be-developed digital means. In another embodiment, controller CO executes instructions stored in firmware or software in a processor or a memory.

In an example, controller CO is configured (e.g., programmed) to perform the functions described herein, and as used herein. The controller CO may include one or more computers, processors, microcontrollers, microcomputers, programmable logic controllers, application-specific integrated circuits, other programmable circuits and the like.

Software may be used to implement or to aid in performing the disclosed concepts. Software functionalities of a computer system involving programming, including executable code, may be used to implement the methods disclosed herein. The software may be code that is executable by controller CO. In operation, the code and possibly the associated data records are stored within the computer and control system or stored externally. Hence, the embodiments discussed herein may involve one or more software products in the form of one or more modules of code carried by at least one machine-readable medium.

As used herein, a machine-readable medium refers to any medium that participates in providing instructions to a processor for execution. Such a medium may take many forms, including, but not limited to, non-volatile media, volatile media and transmission media. Non-volatile media include, for example, optical or magnetic disks, such as any of the storage devices in any computer(s) operating as one of the server platforms discussed above. Volatile media include dynamic memory, such as the main memory of such a computer platform. Physical transmission media include coaxial cables, copper wire and fiber optics, including the wires that comprise a bus within a computer system. Carrier-wave transmission media can take the form of electric or electromagnetic signals or of acoustic or light waves such as those generated during radio frequency (RF) and infrared (IR) data communications.

Common forms of computer-readable media therefore include, for example: a floppy disk, a flexible disk, a hard disk, magnetic tape and any other magnetic medium; a CD-ROM, a DVD and any other optical medium; less commonly used media such as punch cards, paper tape and any other physical medium with patterns of holes; a RAM, a PROM, an EPROM, a FLASH-EPROM and any other memory chip or cartridge; a carrier-wave transporting data or instructions; cables or links transporting such a carrier wave; or any other medium from which a computer can read programming code and/or data. Many of these forms of computer-readable media may be involved in carrying one or more sequences of one or more instructions to a processor for execution.

The controller CO may be configured (e.g., via hardware, software, or a combination of both) to provide enhanced data transfer, data compression and processing techniques known in the art to facilitate the handling and processing of large amounts of data. Examples of such systems and methods are disclosed in U.S. Pat. No. 7,590,996, entitled "Data Path for High Performance Pattern Generator," and in Cramer et al., "Lossless compression algorithm for REBL direct-write E-beam lithography system," in *Alternative Lithographic Technologies II*, edited by Daniel J. C. Herr, Proceedings of the SPIE, vol. 7637, article id. 76371L, (Apr. 2, 2010), which patent and which article are incorporated by reference herein.
Method According to Operation In the operation of microscope 10, IPG 50 generates green diffraction beams 61D of green light 61. These diffraction beams 61D are reflected by beam splitter BS2 to enter the input end 102 of object lens 100. Each diffraction order of green diffraction beams 61D therefore generates a collimated beam that emerges from the objective lens 100. The collimated green diffraction beams 61D overlap at object 122. The overlapping collimated diffraction beams 61D generate a first green fringe pattern or "interference-pattern image" on object 122.

Figure 3B:
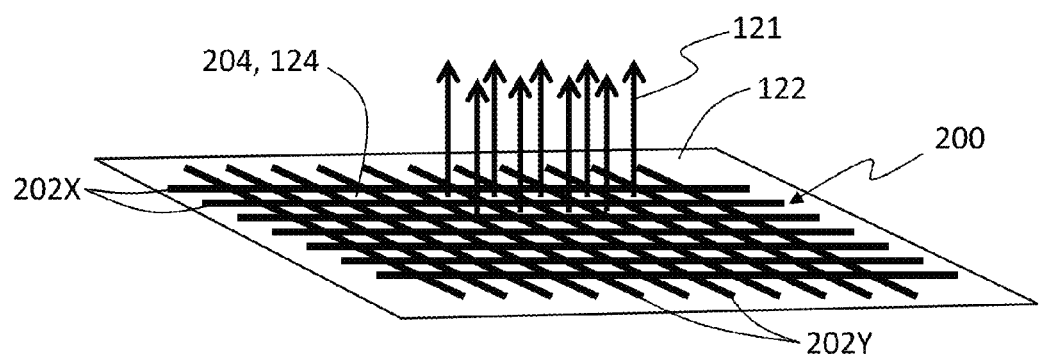
FIG. 3B is a close-up view of a portion of the object, showing the interference-pattern image and the emission areas it defines on the object, with the emitted fluorescent light shown being emitted from the emission areas.

FIG. 3A and FIG. 3B show an example of an interference-pattern image 200 that consists of first and second line interference-fringe patterns 202X and 202Y that are oriented in orthogonal directions and that do not interfere with each other because they originate from separate lasers or because they have orthogonal polarizations, or both. It is also possible to add a third set of interference fringes, and in this case the fringe patterns are oriented at 120° to each other and generated from three separate lasers. An example interference-pattern image 200 at object 122 has the form of a fine X-Y grid.

The phase shifters 84 introduce a path-length change between the two coherently linked, green diffraction beams 61D, thereby causing the resultant interference-fringe patterns 202X and 202Y to shift position normal to the fringe direction. Since the positions of the interference-fringe patterns 202X and 202Y determine the position of the interference-pattern image 200, the phase shifters 84 provide a very quick and easy way to adjust the position of the interference-pattern image, e.g., to compensate for a scanning motion of the stage 110 or any small errors in the stage position.

Figure 5:
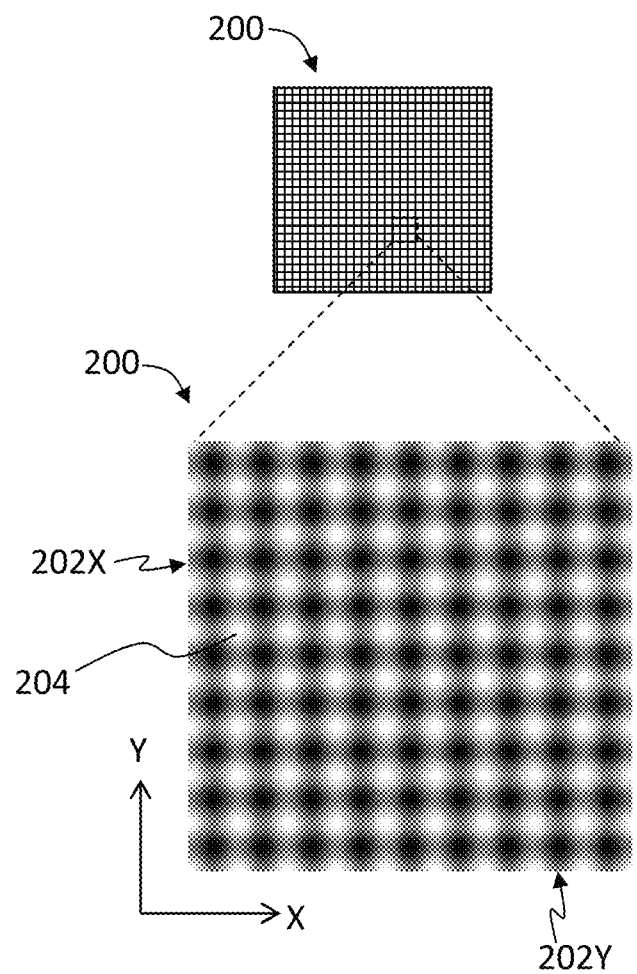
FIG. 5 is a diagram of an example interference-pattern image, including a close-up view that shows the grid pattern formed by overlapping first and second interference-fringe patterns oriented in orthogonal directions.

The objective lens 100 is configured to operate in combination with beam splitter BS2 to focus each of the four green diffraction beams 61D in four symmetrically located positions around the edge of the pupil 106. After passing through the objective lens 100, each of the four green diffraction beams 61D is collimated. The collimated diffracted light beams 61D overlap at object plane OP to form the X-and-Y-grid interference-pattern image 200 shown in FIG. 5. The phase shifters 84 are operably connected to a driver unit 86, which in turn is connected to a control unit (not shown) that synchronizes the fringe positions with the position of the stage 110 during the exposure. A zero-order light-blocking member 88 is arranged along axis $A_G$ and adjacent beam splitter BS2 so that only green light 61 from the four ±1st order green diffraction beams 61D passes through to the beam splitter BS2 and through objective lens 100.

With reference again to FIG. 5, the net result of imaging the four diffracted light beams 61D in the object plane OP is a robust interference-pattern image 200 of equal lines and spaces that stretches across the field of the objective lens 100 in the X- and Y-directions, thereby forming the aforementioned X-Y grid. The "open" areas of the grid are denoted as 204.

With reference again to FIG. 1 and also to FIGS. 3A and 3B, object 122 is also illuminated with blue light 21 from blue light-source system 20. The blue light 21 is generated in blue light-source system 20, is reflected by first beam splitter BS1 and then travels down main axis A1 through third beam splitter BS3, through second beam splitter BS2 and finally through the objective lens 100 to the object 122. The objective lens 100 and blue light-source system 20 are configured such that blue light 21 substantially uniformly illuminates object 122. As noted above, blue camera 140 can be used to view the object 122 for alignment and general viewing purposes. As discussed above, blue light 21 is the activation light that causes the material making up object 122 to give off fluorescent light 121 (see FIGS. 3A, 3B).

Figure 6:
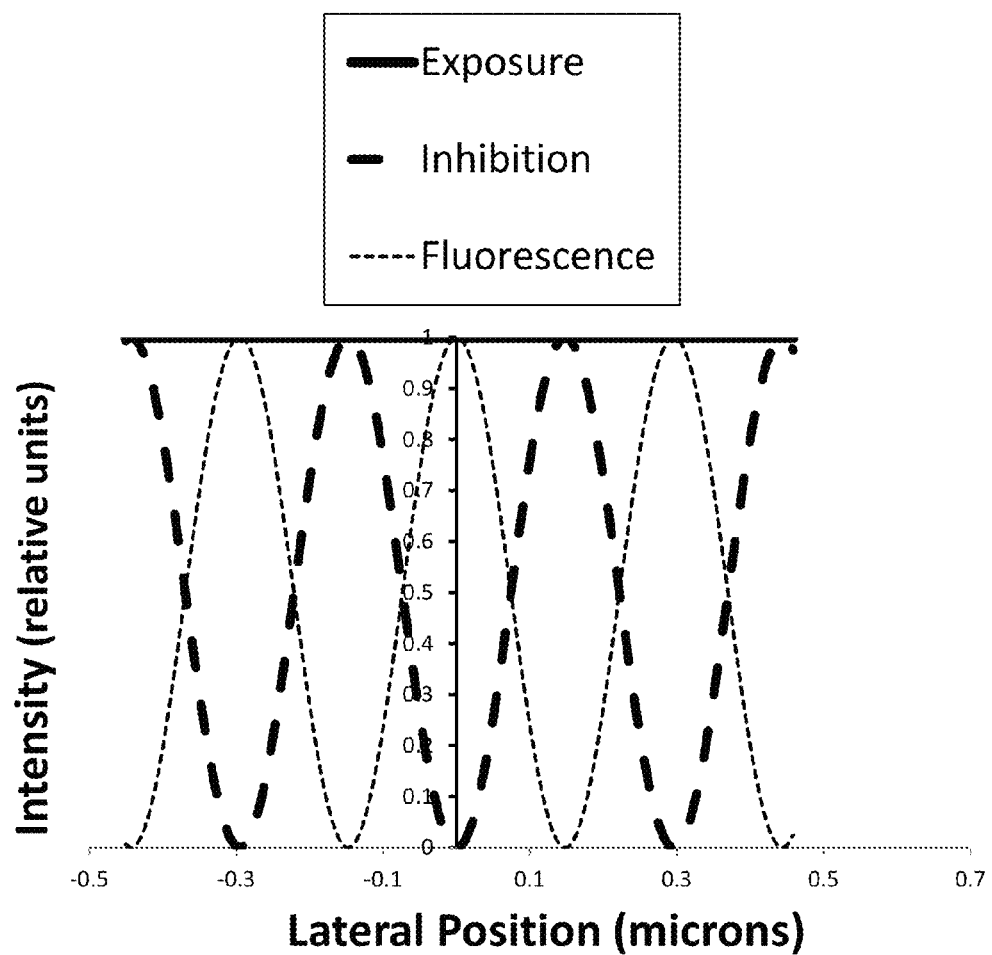
FIG. 6 is a plot of lateral position (microns) versus intensity (relative units), showing an example intensity distribution for the interference-pattern image formed using the inhibition wavelength, the activation light and the fluorescent light.

FIG. 6 is a plot of intensity versus lateral position (microns) for the blue light 21, the interference-pattern image 200 (which is formed by the inhibition green light 61) and the fluorescent (red) light 121. In this case, the intensity of the blue light 21 might be measured in a unit such as W/cm$^2$, and the intensity of the green light 61 is measured in a unit sized so that one unit of red light just cancels one unit of the blue light.

When object 122 is illuminated with only uniform blue light 21, fluorescence over the entire portion of the object 122 would normally result, with the intensity varying depending on how the fluorescent material is distributed over the object. However, superimposed on object 122 is the interference-pattern image 200 that inhibits fluorescence in select areas of the object, namely wherever there is an interference-fringe pattern 202X or 202Y. Thus, object 122 will fluoresce only from areas that correspond to open areas 204 defined by interference-pattern image 200 where the intensity of green light 61 is zero (or almost zero) and there is some fluorescent material present on the object. The areas of object 122 that emit fluorescent light 121 are referred to herein after as "emission areas" and are denoted 124. Emission areas 124 are also referred to as "super-resolution elements." In FIG. 3B, fluorescent light 121 is shown being emitted from emission areas 124, the emission being shown only from a subset of the emission areas for ease of illustration.

Figure 7:
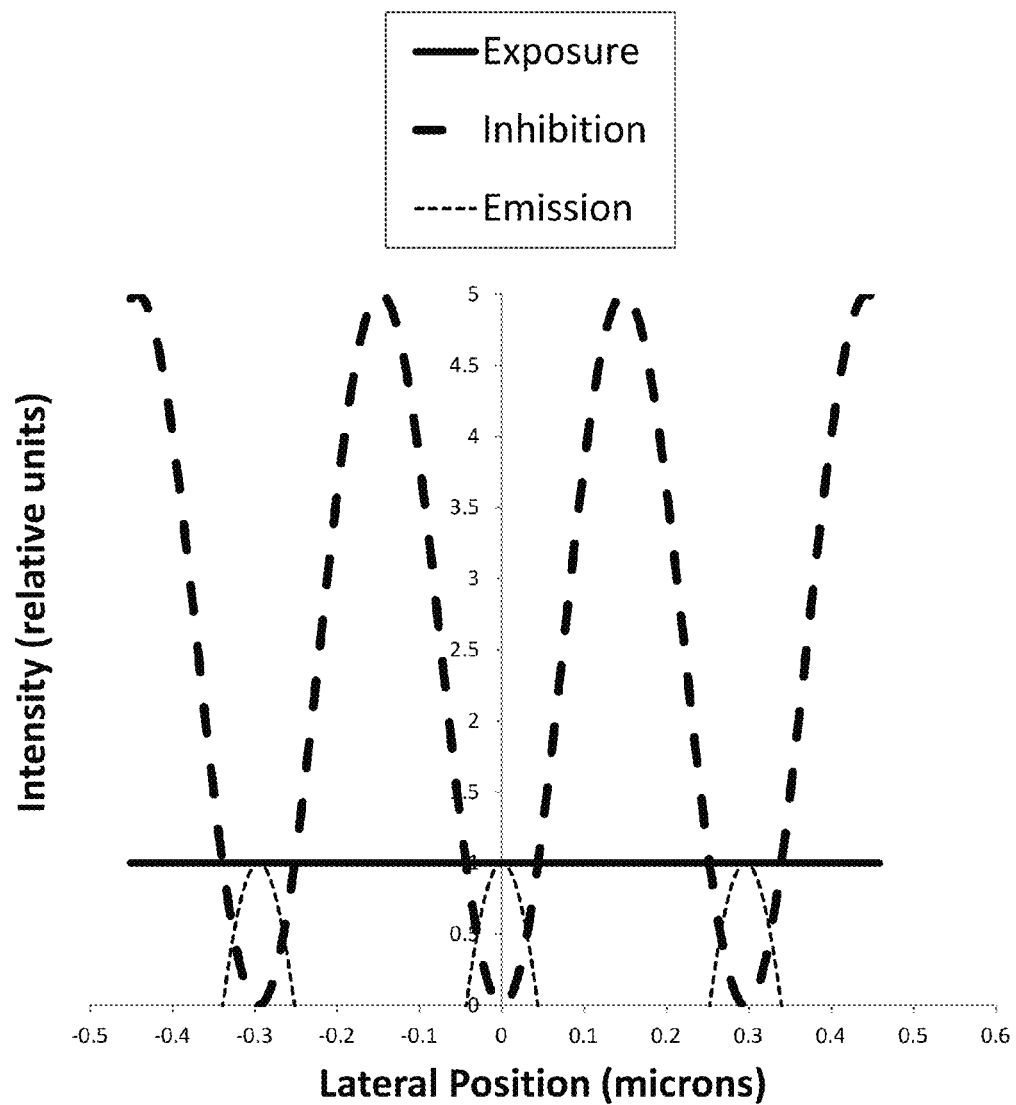
FIG. 7 is similar to FIG. 6 and illustrates an example embodiment where the peak intensity of the inhibition light of the interference-pattern image has 5× the intensity of the activation light.

By increasing the ratio of the green light intensity G to the blue light intensity B, the amount of fluorescence inhibition can be increased, thereby making the open areas 204 smaller and thus the emission areas 124 smaller. An example of this approach is shown in the plot of FIG. 7, where the green-to-blue intensity ratio G/R has been increased to 5:1, and the size of the emission areas 124 has diminished.

The size of the area of fluorescence of object 122 as defined by interference-pattern image 200 is called the image width IW and can be expressed as $IW = \lambda_2 \cdot \arcsin(0.6 \cdot B/cG)^{1/2}/(\pi \cdot NA)$, where $\lambda_2$ is the wavelength of the green light that forms the interference-pattern image, NA is the numerical aperture of the optical system, and the ratio $B/c \cdot G$ is the ratio between the blue light intensity B and the green light intensity $c \cdot G$ used to inhibit the fluorescence generated by the blue signal. The constant c is a proportionality constant so that green intensity G and blue intensity B can be expressed in the same units.

While stochastic analysis can indicate the intensity ranges for green intensity G and blue intensity B over which pictures (images) having reasonable fidelity can be obtained, the maximum value of G can be measured experimentally to within some margin of error during the set-up of the microscope 10 by increasing the green intensity G to null the fluorescence signal.

The equation for the image width IW significantly changes the resolution limits of microscopy from a limit imposed by electromagnetic wave theory (i.e., the Abbe limit) to a limit determined by chemistry or molecular energy states, where intensity ratios determine the limiting resolution.

Figure 8A:
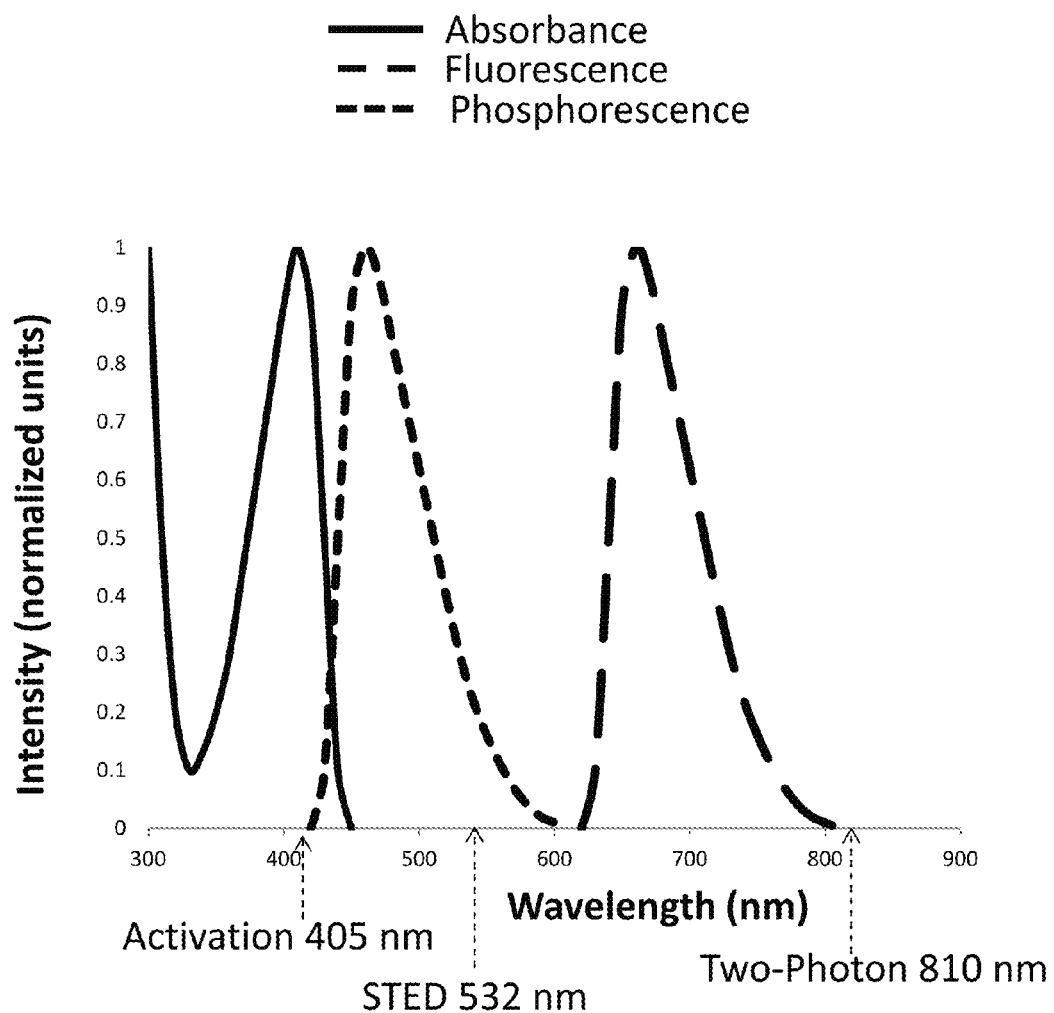
FIG. 8A is a plot of the spectral intensity (relative units) versus wavelength (nm) showing various light excitation and depletion processes.

An example of a typical absorbance and fluorescence spectrum for a two-color fluorescent material that can be used for object 122 is shown in FIG. 8A, which plots the wavelength (nm) versus the spectral intensity (normalized units). Note that there is usually a small overlap between the absorbance and fluorescence spectra and that the absorbance curve also coincides with the excitation spectrum. The short-wavelength end of the absorbance curve can also contain absorption contributions from other components, such as the solvent containing the fluorescent compound. It is generally desirable to avoid the overlap region between the absorbance and emission spectra when choosing the activation wavelength $\lambda_1$, which is indicated by the arrow labeled "Activation 405 nm."

The green (inhibition) wavelength $\lambda_2$ is generally located between the peak of the fluorescence emission and the long-wavelength cutoff, which is just beyond 600 nm in FIG. 8A. There are usually competing pathways for dissipating the energy given to the fluorescence molecules by the activation wavelength $\lambda_1$, including possibly phosphorescence via an intersystem crossing and subsequent relaxation to the ground state, which usually has a much longer time constant and a longer wavelength emission spectrum. In FIG. 8A the inhibition wavelength is indicated by the arrow labeled "STED 532 nm."

The other possibility for excitation is to employ two photons, each having a wavelength twice as long as the single-photon activation wavelength $\lambda_1$. Ensuring a reasonable probability that two photons will arrive at the same place at the same time requires very high intensities and therefore a small beam area. Excitation with two photons is used for single-beam, three-dimensional lithography because it enjoys the added advantage that the fluorescent material is usually quite clear at the two-photon wavelength. The two-photon wavelength in FIG. 8A is indicated by the arrow labeled "Two-Photon 810 nm."

A model based on crossed interference grid patterns created with inhibiting light 61 of wavelength $\lambda_2$ to trim the fluorescent light 121 emitted from emission areas 124 of substrate 120 that is uniformly illuminated with blue exposure light 21 may be derived as follows.

First, it is assumed that the intensity of the blue (activation) light 21 is B and that the effective intensity of the green (inhibiting) light 61 is c·G. The minimum period P of the green fringe pattern in the interference-pattern image 200 is given by P=$\lambda_2$/(2·NA), where NA is the numerical aperture of objective lens 100. The periodic fringe-pattern intensity $I_G(x)$ of the interference-pattern image 200 is therefore described by $I_G(x)=c·G(\sin(\pi x/P))^2$, where x measured from the center of the fringe null point.

The center of the trimmed fluorescent pattern is located at zero, and the two edge locations occur where the inhibition fringe intensity is equal to some fraction of the blue intensity, which is usually taken as 0.4B but which depends on the exposure level. Solving for x when the intensity has been reduced to 0.4B yields:

$$I(x)=0.4·B=c·R·(\sin(2·\pi·x·NA/\lambda_2))^2$$

$$x=(\lambda_2/2·\pi·NA)·\arcsin((0.6·B/c·G)^{0.5})$$

The resultant image width IW' as measured at the zero intensity level is therefore given by 2x, or:

$$IW'=(\lambda_2/\pi·NA)·\arcsin((0.6·B/c·G)^{0.5})$$

Figure 8B:
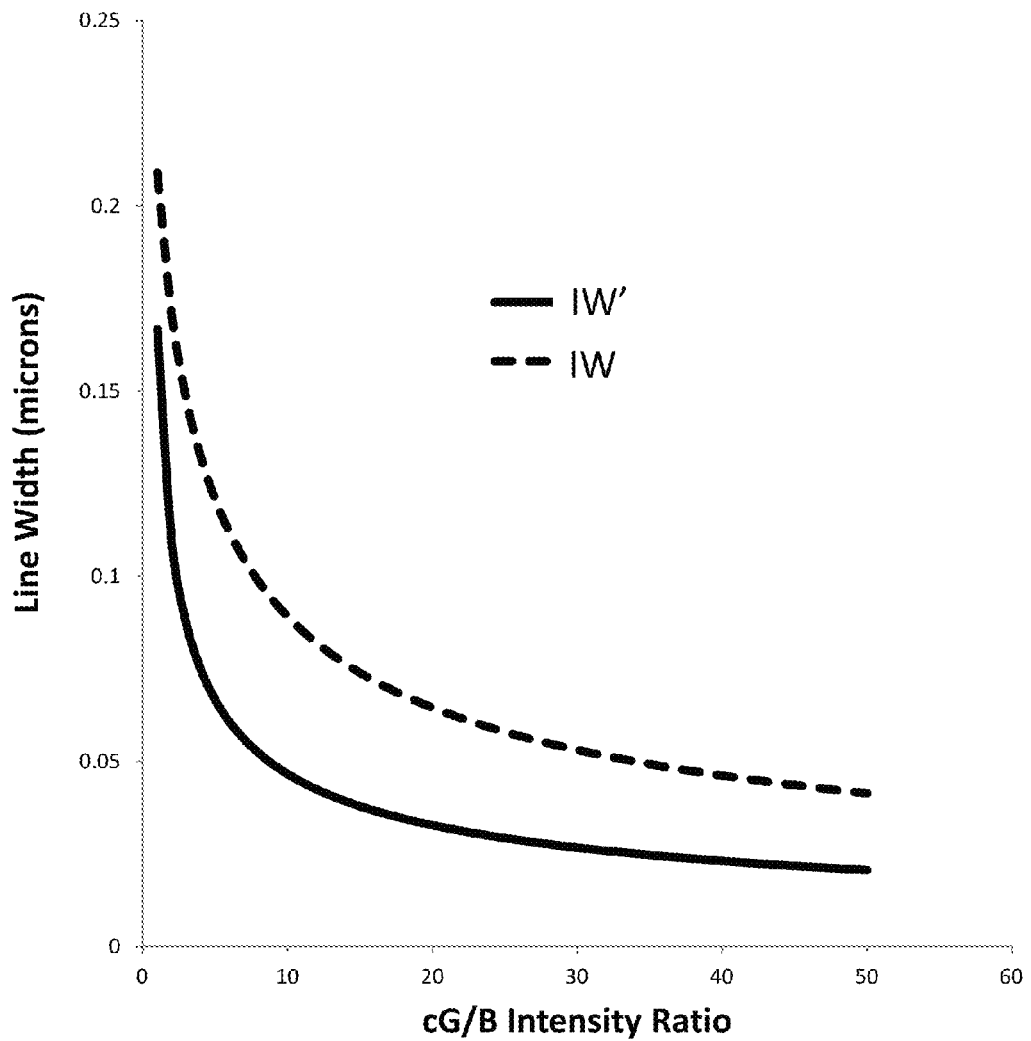
FIG. 8B is a plot of image width (microns) versus the red-to-blue intensity ratio R/B for two image widths IW and IW' as calculated by two different formulas.

FIG. 8B plots the c·G/B intensity ratio versus image width (microns) and compares the amount of image-pixel narrowing as predicted by the above expression for the image width IW' and the prior art expression for image width IW given by IW=$\lambda_2$/((2·NA)(1+cG/B)$^{1/2}$). In both cases, the NA of the objective lens 100 is assumed to be 0.9 and the inhibition wavelength is assumed to be 532 nm.

Unless the cG/B ratio is one or greater, the resultant image intensity does not reach zero and is therefore undefined by this formula. The difference between the two formulas may be partially explained by the assumptions used to derive the expression for IW.

Figure 9A:
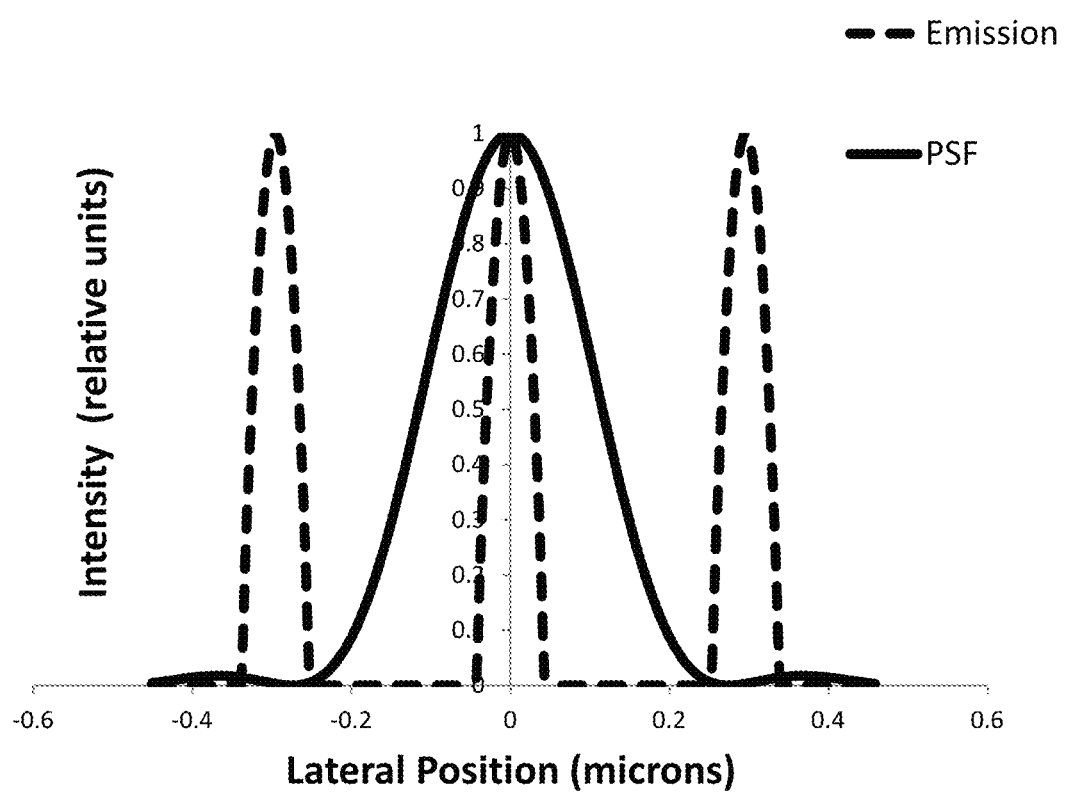
FIG. 9A is a plot of intensity (relative units) versus lateral position (microns) showing the fluorescence emission at 3 points on the substrate for an R/B ratio of 5:1 and the point spread function (PSF) for a single point on the substrate.

FIG. 9A is a plot of the intensity (normalized units) versus lateral position (microns) and shows a comparison between the point spread function (PSF) of microscope 10 for a single-point source and the geometrical size and position of three, small fluorescence emission areas from three, adjacent emission areas 124 on object 122, assuming no pupil diffraction. The emission areas 124 are sub-resolution, i.e., they are too small to be resolved by objective lens 100, where resolution is measured relative to the Abbe Limit.

Figure 9B:
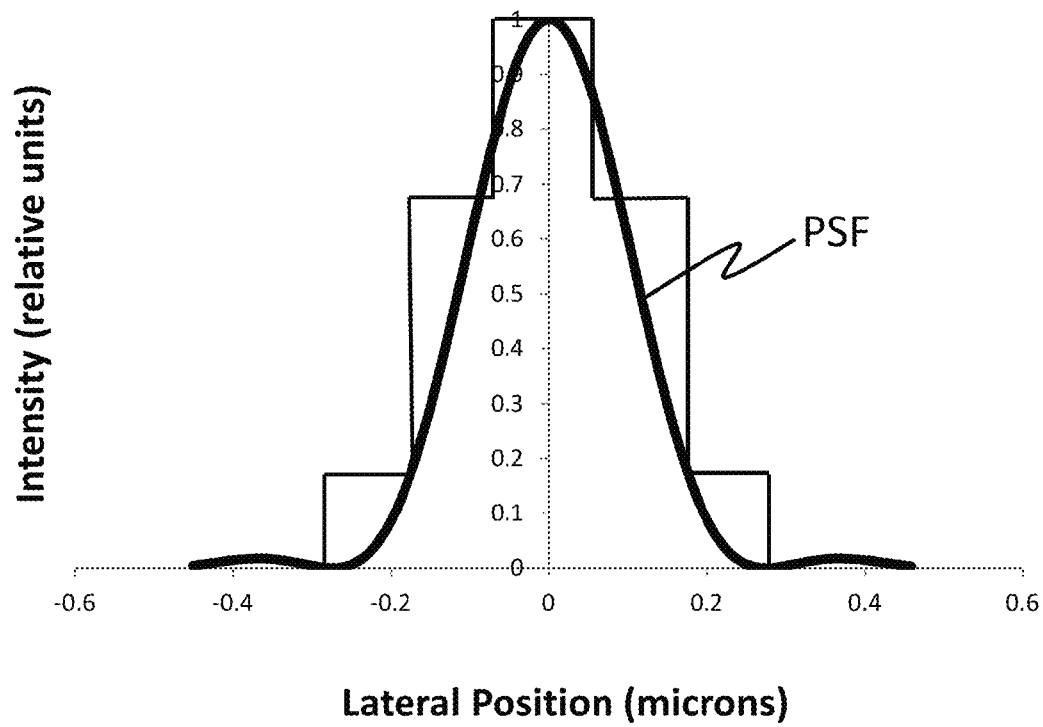
FIG. 9B is similar to FIG. 9A and also shows the photodetector signals from the detector elements in the immediate vicinity of the image from a single point on the substrate, as well as the associated PSFs.

The PSF of microscope 10 is defined mainly by the NA of objective lens 100 and is the image size at the detector plane DP when imaging an infinitely small spot or point on object 122. The actual image size at the detector plane DP is a convolution of the actual emission profile of fluorescent light 121 at the object plane OP with the PSF. FIG. 9B is similar to FIG. 9A and shows the stepped signal that represents the output of detector elements DE of photodetector 154 that sample the image. Because the PSF of the objective lens 100 is usually much wider than the emission profile of the fluorescent light 121 from a given emission area 124, the convolution of the PSF and the emission profile are well approximated by the PSF.

Although convolution always makes the resultant image slightly wider, the effect is hardly noticeable if the emission from emission area 124 is appreciably narrower than the PSF. FIGS. 9A and 9B show that the geometrical size of the emission area 124 of object 122 is small in comparison to the actual image at the detector because of diffraction effects. Thus, to reconstruct the object image and preserve the resolution obtained by forming small emission areas 124, it is necessary to de-convolve the signals from photodetector 154 for each captured image or "snapshot."

The de-convolved intensities and positions from multiple snapshots of object 122 as captured by fluorescence camera 150 are then used to construct a super-resolution image of object 122. Thus, in an example, controller CO is employed to record the images (signals) obtained for each interference-pattern image position 200, with different interference-pattern image positions having different positions for interference-fringe patterns 202X and/or 202Y. The controller CO then calculates the corresponding intensity for each emission area 124 defined by interference-fringe patterns 202X and 202Y, taking into account any light that might be diffracted from emission area 124 into the adjacent emission area. The resultant intensities from an entire series of snapshots for the emission area 124 on object 122 are then combined to create the single high-resolution picture of object 122.

To preserve the fine details of object 122, in an example the object is imaged on a pixel-by-pixel basis in each frame, and each frame is obtained by shifting the emission areas 124 over a two-dimensional grid and measuring the corresponding intensities. For example, emission areas 124 on object 122 can be trimmed down to a 30-nm diameter by increasing the intensity G of the surrounding green interference-fringe patterns 202X, 202Y relative to the blue activation intensity B. The image of this small patch at photodetector 154 as formed by a 0.9 NA objective lens 100 would represent a conventional image pixel and would be limited to something bigger than the diffraction-limited image size of $\lambda/(2 \cdot NA)$, until it is de-convolved.

Assuming an average fluorescence emission wavelength of 550 nm and an NA for objective lens 100 of 0.9, the image size IW' would be roughly the diffraction-limited size of 306 nm, plus a small contribution from the size of the emission area 124 of 30 nm, for a total size of about 320 [320→336?] nm. Clearly such an image cannot reveal any detail in the 30-nm emission area 124; it simply reveals the intensity and the approximate position of one small object region. The actual position is determined based on knowledge of the positions of the interference-fringe patterns 202X, 202Y that define the emission area 124. The fine details of the object 122 are obtained in sequence by moving the emission area(s) 124 around the object, capturing images of the emission areas as image pixels and measuring the intensity and position of each image pixel. With a suitable photodetector 154, the intensities corresponding to thousands or even millions of emission areas 124 can be measured simultaneously. It is helpful if the signal from each emission area 124 can be easily separated from those from neighboring emission areas.

Although the detector image signal shown in FIG. 9B accurately represents the image (signal) at the detector plane DP from a single emission area 124 on object 122 (i.e., from a single image pixel), it does not represent the signal produced by the photodetector 154, where a number of adjacent emission areas contribute signals. Because the signals from adjacent emission areas 124 overlap at photodetector 154, each detector signal SD contains components from adjacent emission areas. In addition, because each detector element DE of photodetector 154 has a finite size, the resultant detector signal SD is integrated over an area and reports an average value, as shown by the stepped curve in FIG. 9B.

If the PSF of microscope 10, the size of emission areas 124 on object 122, and the size of detector elements DE that make up photodetector 154 are each known, then the detector signals SD can be de-convolved and the intensity of the signal coming from a specific emission area on object 122 can be accurately determined. It is desirable to choose a magnification for objective lens 100 that results in more than two detector elements DE spanning the distance between each emission area 124 on object 122.

The super-resolution image of object 122 is formed by combining multiple images (signals) captured by fluorescence camera 150. Each of the multiple images includes image pixels that are images of corresponding emission areas 124. FIG. 10 is a schematic diagram that shows how trimming the size of emission areas 124 (denoted as dots numbered 1 through 9) results in a very sparse coverage of object 122. The first captured image is for exposure areas 124 that are labeled 1. Successive snapshots with a shifted interference-pattern image 200 are used to cover more space on object 122 via the indicated scan path. The exposure areas 124 associated with subsequent snapshots 2, 3 . . . 9 are indicated by dots labeled 2, 3 . . . 9. Improving the resolution by a factor of 3 requires 9 snapshots, and more generally, an improvement by a factor of n requires $n^2$ snapshots.

Figure 10A:
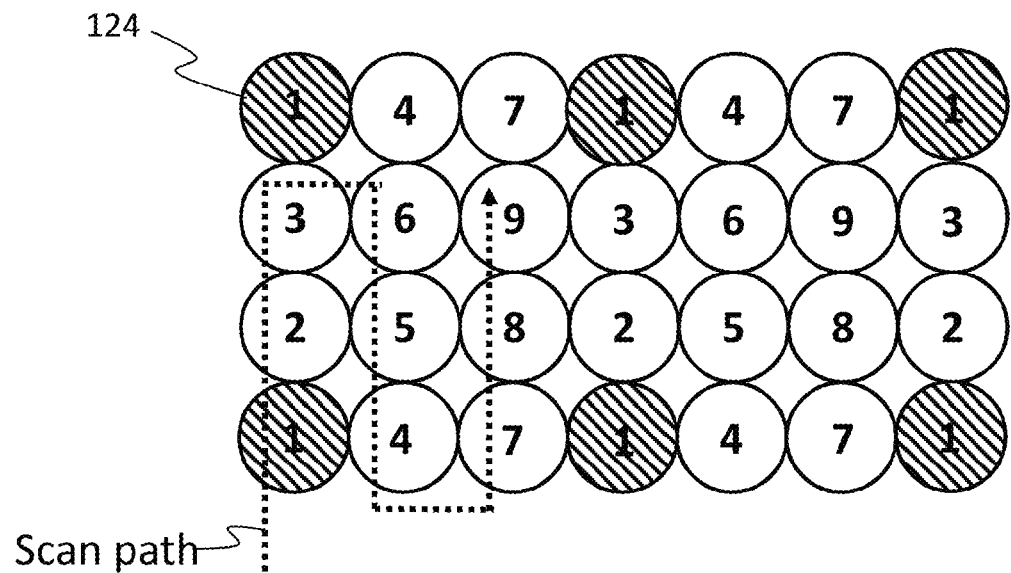
FIG. 10A is a schematic diagram illustrating how a sparse pattern of samples from an image requires multiple exposures to obtain a complete picture of the sample.
Figure 10B:
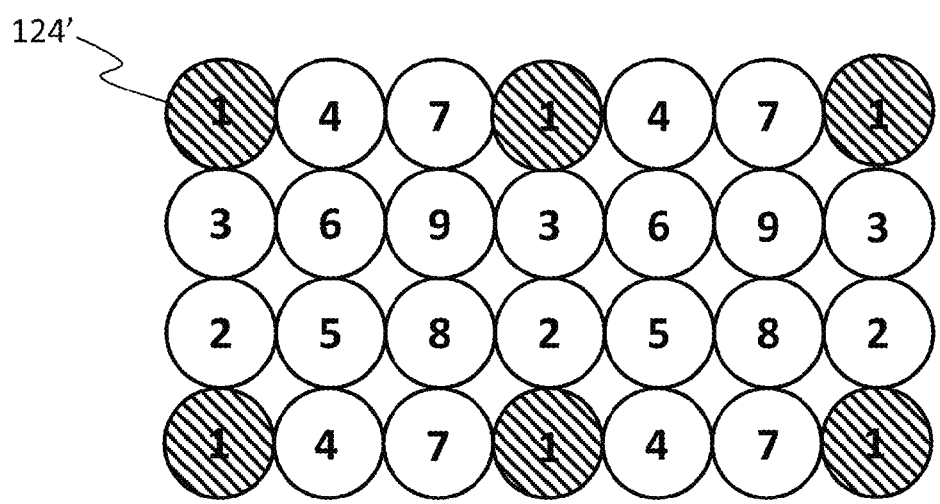
FIG. 10B is the same as FIG. 10A but shows the corresponding captured images and the respective image pixels for the exposure areas that are imaged over the scan path.

FIG. 10B is the same as FIG. 10A but shows the corresponding captured images and respective image pixels 124' for the exposure areas 124 that are imaged over the scan path.

Figure 10C:
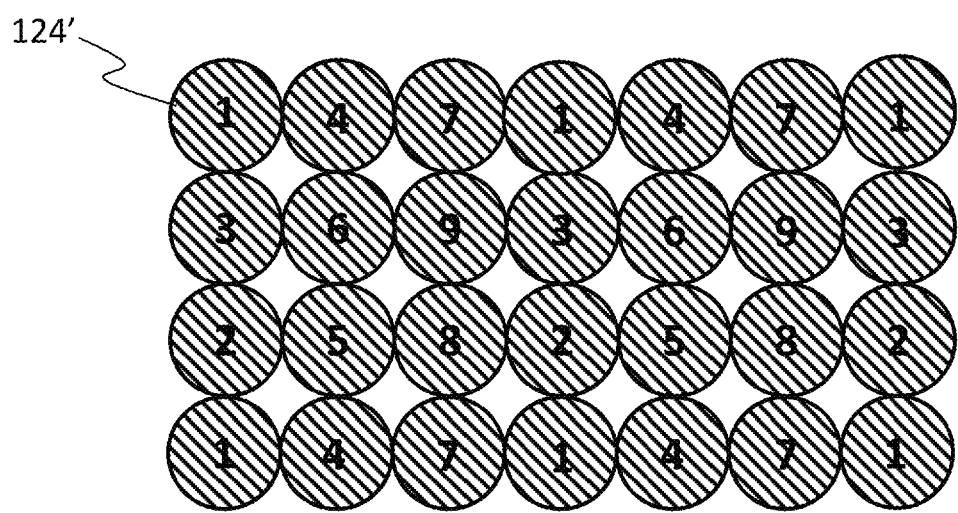
FIG. 10C is similar to FIG. 10B and shows the final super-resolution image as the combination of the $n^2=9$ sparse images.

FIG. 10C shows the final super-resolution image as the combination of the $n^2=9$ sparse images (snapshots). Each of the image pixels 124' have a corresponding intensity based on the measured intensity of the corresponding emission area 124 on object 122.

Untangling the Signals

Figure 11:
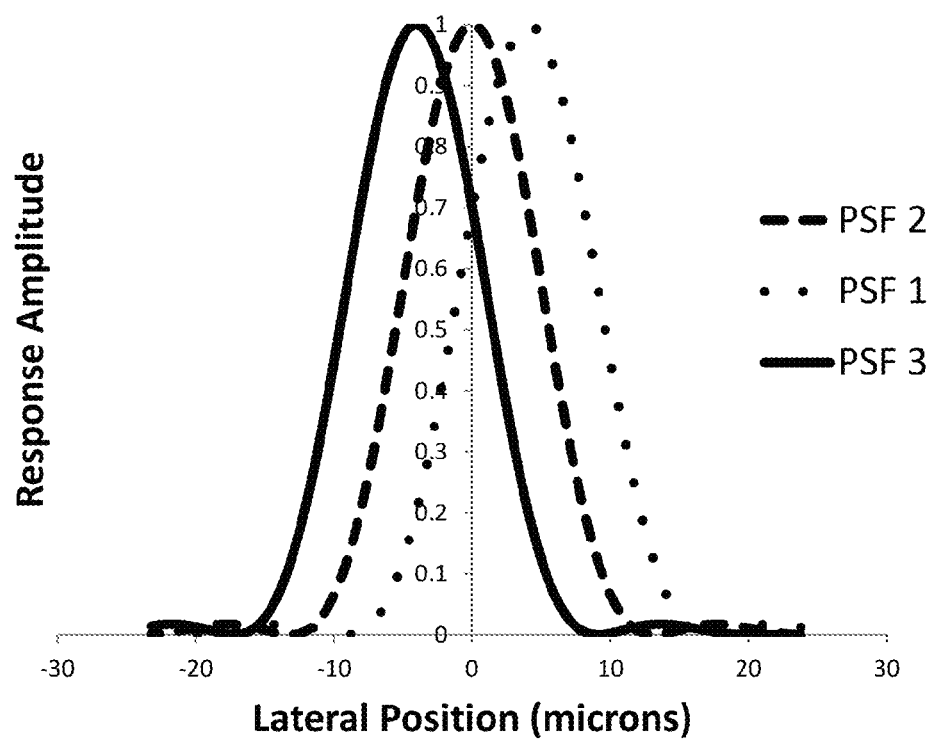
FIG. 11 is a plot illustrating how three adjacent point spread functions might in practice overlap.

The character of detector signal SD is determined by the PSF of the objective lens 100 using the fluorescence spectrum and the size of emission area(s) 124 formed on object 122. A reasonable approximation for the fluorescence spectrum can be obtained using the green (inhibition) wavelength $\lambda_2$. FIG. 11 shows the shape of the PSF and the overlap of three PSFs associated with three adjacent emission areas 124. In this illustration, the fluorescence spectrum is assumed to be centered at 532 nm and the NA of objective lens 100 is assumed to be 0.9.

Figure 12:
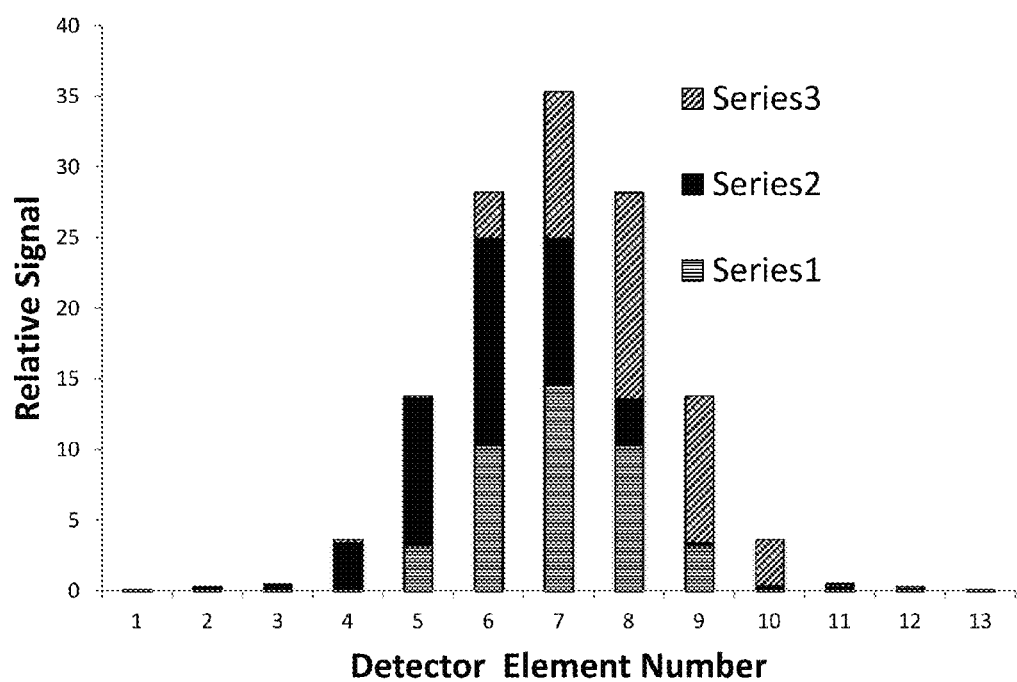
FIG. 12 is a plot of the relative photodetector signal versus detector element number for the three adjacent point spread functions, illustrating the signal variation from one detector element to the next.

The Nyquist theorem states that to recover all the information in the spatial frequency spectrum a minimum of two detector elements DE is required to span the distance corresponding to the diffraction limit. It is assumed that there are 2.6666 detector elements DE for each space between adjacent image pixels 124'. FIG. 12 is a graph that shows the proportion of the signal SD from each image pixel that falls on each detector element DE.

In FIG. 12, the contribution from the central image pixel is represented by the Series 1 data. FIG. 12 does not take into account the emission areas 124 in the other dimension. But it is intuitively clear that if the position of each emission area 124 is accurately known, along with the proportional contributions from all the neighboring emission areas, then the intensity for each emission area can be derived. FIG. 12 is a convolution of the PSF and the emission areas 124 and also includes the effect of the overlap between the convolved signals. Each detector signal SD is converted to a numerical value as represented by the height of the corresponding bar.

Numerical Example

A numerical example is now presented as based on the following assumptions:
Size of photodetector 154 (detector array): 1,024 by 1,024 detector elements DE
Size of individual detector element DE: 3×3 microns
Green (inhibition) wavelength $\lambda_2$=532 nm
Blue (activation) wavelength $\lambda_1$=405 nm
Objective lens NA=0.9
Resolution required=25 nm
The green and blue intensity values c·G and B can be obtained from the equation for resolution, namely: IW'=$(\lambda_2/\pi \cdot NA)$ ·arcsin$((0.6B/cG)^{0.5})$ $$25 \text{ nm}=(532 \text{ nm}/\pi \cdot 0.9)\text{arcsin}((0.6 \cdot B/cG)^{0.5})) \rightarrow c \cdot G/B=33.8$$

To obtain a resolution of 25 nm, it is necessary to have a green-to-blue intensity ratio cG/B=33.8. This assumes that the fluorescence generated by one watt of 405-nm blue light will be suppressed by the equivalent of one watt of 532-nm green light. The equivalence depends on the value of the constant c.

This improvement in resolution is achieved by reducing the size of the emitting areas 124 on object 122 and is not directly seen on photodetector 154. The detector image is limited by the PSF of the objective lens 100 to a width of about $\lambda_2/(2 \cdot NA)$. Thus, the image pixels 124' for adjacent emission areas 124 overlap considerably at photodetector 154, making it necessary to employ an algorithm to untangle them completely.

As noted above, it is necessary to have a minimum of two, and usually more than two, detector elements DE for a given image pixel 124'. There exists a special case where only one detector element DE is required for every image pixel 124'. But this requires that each image pixel 124' be perfectly centered on each detector element DE. If more than two detector elements DE are used to span the space between adjacent image pixels 124', then there is no need to center the image pixels on corresponding detector elements, or to have an integer number of detector elements from one image pixel to another.

For example, if photodetector 154 has 1,024 by 1,024 detector elements DE, and if it is desired to employ three detector elements between adjacent image pixels 124', then the resulting field size on object 122 will be 1024×532 nm/(3×2×0.9)=101,000 nm=101 μm. The magnification M between detector plane DP and the object 122 depends on the size of detector elements DE. For example, if detector elements DE are 5 microns on a side, then the magnification M is given by the ratio of the size of the photodetector 154 to the size of the field on the substrate 120.

Thus, $$M = 1024 \times 5 \, \mu m / (101 \, \mu m) = 50.7.$$

Constructing the High-Resolution Image

In general, most images captured by fluorescence camera 150 will not have all the information needed for a complete de-convolution, i.e., the determination of the position and intensity of each emission area 124. Therefore, a complete de-convolution of an image is usually impossible. However, there are special cases where a complete or almost-complete de-convolution is possible. The image obtained with microscope 10 is one of the special cases. The image from microscope 10 is an image of fluorescing spots (i.e., the captured image contains image pixels 124'), which are much smaller than the resolution of the imaging system and overlap each other at detector plane DP. The emission areas 124 are much smaller than the PSF of microscope 10. Therefore, the shape (intensity distribution) of an image pixel 124' looks almost identical to the PSF.

Even if the position de-convolution (or equivalently, the determination of the center of a given emission area 124) can be performed quickly, it still takes a finite amount of time. It is therefore helpful to have a method for minimizing the frequency of the position de-convolution operation. Thanks to the fact that the shape of the super-resolution image in microscope 10 is simply the shape of the PSF and its position can be perfectly stationary on the detector plane DP, the de-convolution operation can be limited to a single time. That is, as long as every super-resolution image is perfectly stationary at the detector plane DP, the position de-convolution operation needs to be performed only once because the result of the position de-convolution, i.e., the center location of each image pixel 124', can be stored in memory and used repeatedly.

Thus, any real-time position de-convolution can be avoided in microscope 10, with the advantage that the demand on computational resources is very minimal. If microscope 10 has imaging stability issues, then position de-convolution can be performed from time to time to update the center position of each image pixel 124' at detector plane DP. This occasional updating of the position information of image pixels 124' increases the demand on computational resources. However, as long as microscope 10 is built with stability in mind, the demand on computational resources is expected to be quite moderate.

To achieve precise positional resolution of the emission areas 124 and their corresponding image pixels 124', the de-convolution needs to be not only complete but also very precise. Conventional de-convolution algorithms can be applied directly to the photodetector image as embodied in detector signal SD, but these methods tend to be too computationally intensive and cannot deliver a precise result.

Consequently, microscope 10 as disclosed herein employs a novel de-convolution method based on the realization that emission areas 124 are discrete and their positions are known to be the center of "holes" in the crossed interference-fringe patterns 202X and 202Y that constitute interference-pattern image 200. This makes it possible to employ separate processes to determine the positions and intensities of emission areas 124. The de-convolution of the image pixels 124' is reduced to a relatively simple regression process that is also more robust than conventional de-convolution processes.

Therefore, a complete and precise de-convoluted result is obtainable using the regression method disclosed herein. In the regression method, a computer (i.e., controller CO) constructs a trial image by incoherently superposing all the PSFs located at all the known positions of emission areas 124 with trial emission-area intensities. Then, a merit function is computed. The merit function is the difference between the measured real image and the computer-generated trial image. The regression process precisely determines the intensities of all emission areas 124 by varying them until the merit function is minimized. The precise emission-area intensity information, together with the known emission-area position information, yields the final result of the new de-convolution (i.e., regression) process.

The fact that the PSF can vary across the image field does not pose a problem because it can be absorbed in a template function. Using a variable template function across the field during the regression process makes it possible to avoid having to change the regression algorithm. The variation of the PSF across the image field can be accurately determined through a direct measurement of many PSFs across the field or through the measurement of aberrations in objective lens 100 and fluorescence camera 150 across the field.

Distortion in the captured image can also be accounted for. The distortion can be measured by imaging an accurate grid pattern or by measuring the interference-pattern image formed by green (inhibition) light 61. The measured distortion can be incorporated into the regression as a coordinate transformation matrix.

If the sampling interval, or equivalently the size of detector elements DE, is small enough to be comparable to the size of emission areas 124, then all that is required to determine the intensity of each image pixel 124' is to perform the regression process. In practice, the size of detector elements DE will be comparable to the size of the PSF for many reasons. In addition, there will be some unknown amount of misalignment between the image pixels 124' and photodetector 154 due to some unavoidable instability in the optics that constitute microscope 10.

In this case, to get an accurate result from the regression process, an accurate sub-resolution interpolation operation on the coarsely sampled image data (i.e., the location of the center of each image pixel 124') is performed to determine the image pixel position to a small fraction of the size of detector elements DE.

None of the conventional sub-resolution interpolation schemes will be accurate enough if the detector-element size is comparable to the PSF or is only a small fraction of the PSF. Modeling has shown that an FFT-based sub-resolution interpolation yields a better result by a couple orders of magnitude than conventional interpolation methods, as long as the size of detector elements DE is the same or smaller than the Nyquist size. According to the Nyquist theorem, the size of detector element DE must be smaller than the minimum wavelength divided by 4NA. A detector-element size that is 20% smaller than the Nyquist size is adequate when using an FFT-based sub-resolution interpolation method.

Figure 13A:
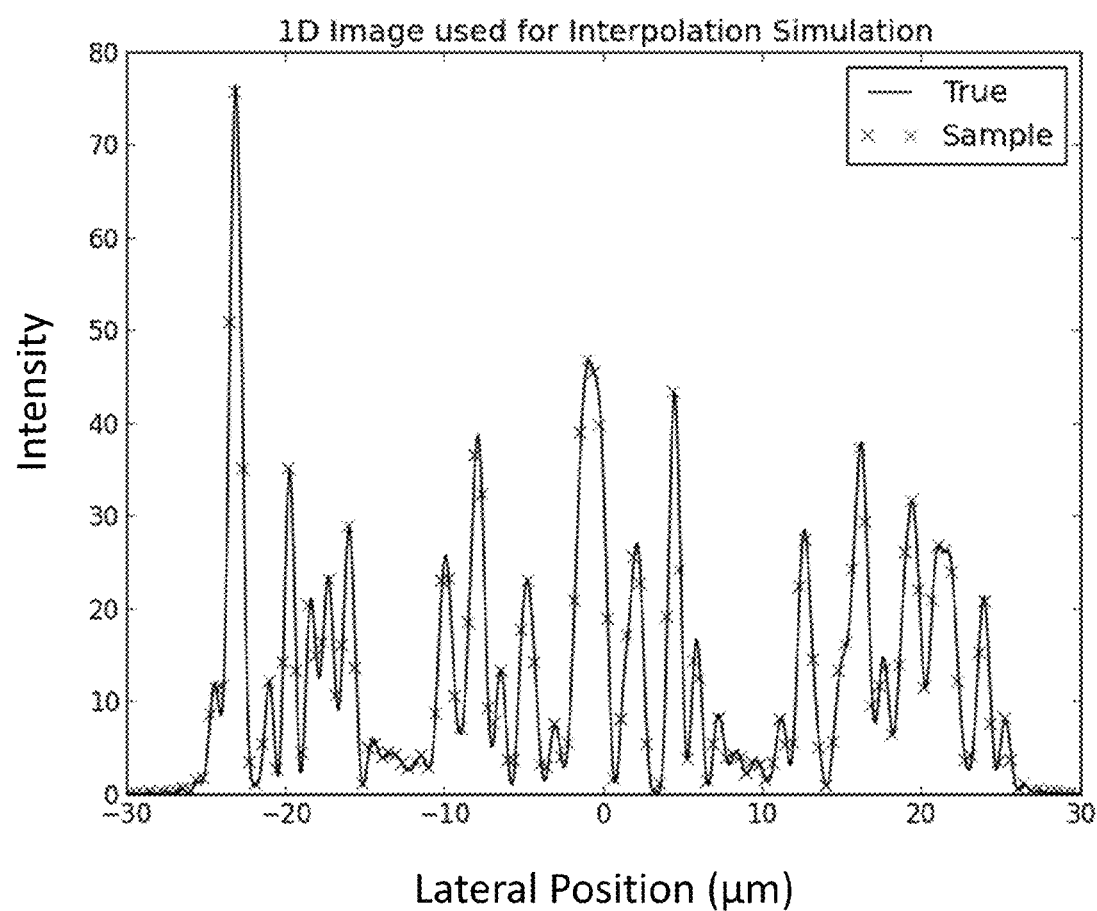
FIG. 13A is a representative cross section of the intensity variation across an image that is sampled on a regular grid.
Figure 13B:
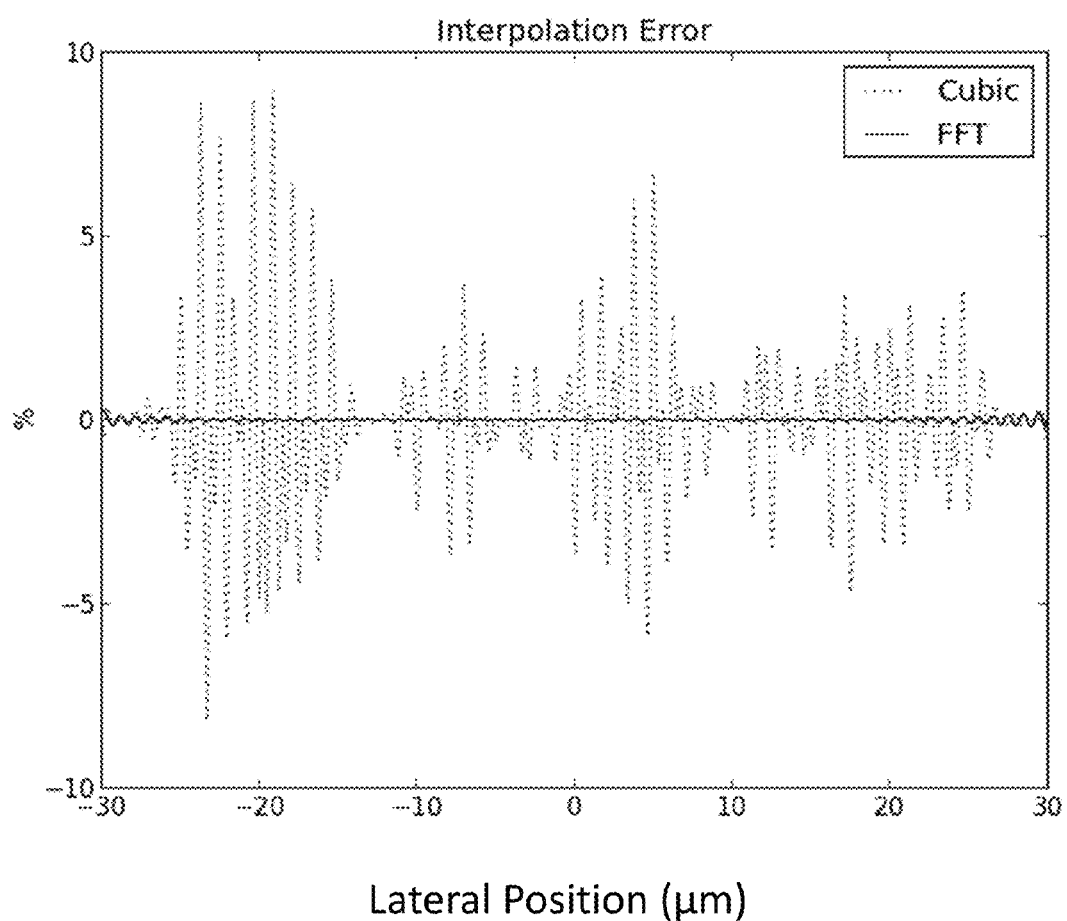
FIG. 13B plots the error (%) versus lateral position using two different methods of interpolating the signal between the sample points.

FIG. 13A is a plot of lateral position (microns) versus intensity from an actual object image that has been periodically sampled. FIG. 13B is a plot of the % error versus lateral position for two different signal reconstruction methods; one based on a cubic interpolation and the other based on an FFT interpolation. The sharp peaks in the image profile of FIG. 13A are not finely sampled by the sample points indicated by the "x" marks. However, the FFT-based interpolation determined all the intermediate values between the sampling points very accurately, as indicated in the error plot of FIG. 13B.

Accurate image synthesis requires that the image position of each image frame be determined precisely, i.e., to the level of a small fraction of the detector element. To determine the image position to this level, the image intensity needs to be measured or computed with accuracy compatible with sub-detector-element resolution. Measuring the image intensity with this resolution is not practical using conventional techniques because the system throughput will be reduced tremendously.

A more practical way of obtaining sub-resolution image-intensity values is by sub-resolution interpolation of the image data. A new interpolation method needs to be devised. The aforementioned FFT-based interpolation method is a natural choice because it is not only fast but also very precise. This method also allows filtering of high-spatial-frequency noise because all the true image signals are band-limited. Usually, the precision of this interpolation method is limited by un-filterable noise. With this method, the interpolation errors are pushed toward the boundary of the image. Therefore, this method provides extremely high interpolation precision except for the extreme boundary areas.

De-Convolution

The intensity seen at any point in the image $I_0(x, y)$ captured by photodetector 154 is the sum of all the overlapping point spread functions of the nearby emission regions:

$$I_0(x, y) = \sum_{j=1}^{n} q_j h(x, y; x_j, y_j): \text{Image model} \quad (1)$$

where $q_j$ is the unknown intensity of $j^{th}$ source that needs to be determined, and $h(x,y;x_j,y_j)$ is the known point spread function for $j^{th}$ source located at $(x_j,y_j)$.

It is helpful to define an error function E that is proportional to the difference squared between the intensity $I(x, y)$ measured at photodetector 154 and the actual intensity $I_0(x, y)$ of the corresponding emission area 124.

$$E \equiv \int\int [I(x, y) - I_0(x, y)]^2 dxdy: \text{Error function for least square regression} \quad (2)$$

$$= \int\int \left[I(x, y) - \sum_{j=1}^{n} q_j h(x, y; x_j, y_j)\right]^2 dxdy \quad (2-1)$$

where $I(x, y)$ is the measured image intensity

All the values of source intensity that minimize the error function need to be found. This kind of problem generally requires numerical regression. However, for the current case, the error function, equation (2-1), is simple enough that the regression can be done analytically.

The minimum value of the error function happens in the n-dimensional source-intensity space where its gradient is zero. Therefore, $$\frac{\partial E}{2\partial q_i} = -\int\int h(x, y; x_i, y_i)\left[I(x, y) - \sum_{j=1}^{n} q_j h(x, y; x_j, y_j)\right]dxdy \quad (3)$$

$$= -\int\int h(x, y; x_i, y_i)I(x, y)dxdy + \quad (3-1)$$

$$\sum_{j=1}^{n} q_j \int\int h(x, y; x_i, y_i)h(x, y; x_j, y_j)dxdy$$

$$= -b_i + \sum_{j=1}^{n} a_{ij}q_j \quad (3-2)$$

$$= 0 \text{ for every emission area 124 ("source")}$$

where $a_{ij} \equiv \int\int h(x, y; x_i, y_i)h(x, y; x_j, y_j)dxdy \quad (3-3)$ $$= a_{ji}: \text{PSF co-variance}$$

$$b_i \equiv \int\int h(x, y; x_i, y_i)I(x, y)dxdy: \text{PSF-image inner product} \quad (3-4)$$

Define $$Q\begin{bmatrix} q_1 \\ q_2 \\ \vdots \\ q_{n-1} \\ q_n \end{bmatrix}: \text{Source intensity vector} \quad (4)$$

$$A\begin{bmatrix} a_{11} & a_{12} & \cdots & a_{1(n-1)} & a_{1n} \\ a_{21} & a_{22} & \cdots & a_{2(n-1)} & a_{2n} \\ \vdots & \vdots & & \vdots & \vdots \\ a_{(n-1)1} & a_{(n-1)2} & \cdots & a_{(n-1)(n-1)} & a_{(n-1)n} \\ a_{n1} & a_{n2} & \cdots & a_{n(n-1)} & a_{nn} \end{bmatrix}: \quad (4-1)$$

PSF covariance matrix $(a_{ij} = a_{ji})$ $$B\begin{bmatrix} b_1 \\ b_2 \\ \vdots \\ b_{n-1} \\ b_n \end{bmatrix}: \text{PSF-image inner-product vector} \quad (4-2)$$

Then, equation (3-2) becomes equivalent to the following matrix equation:

$$AQ=B \quad (5)$$

From equation (5), the source intensity vector becomes:

$$Q = A^{-1} B \quad (6)$$

Thus, all the source intensities can be determined quickly through a well-known matrix manipulation. The computation does not require any time-consuming numerical regression. A more complete explanation of the Regression analysis technique is provided in chapter 14 of *Probability, Statistical Optics, and Data Testing: A Problem Solving Approach* by B. R. Frieden (New York: Springer-Verlag, 1983).

In general, a complete de-convolution of the individual intensities composing an image is impossible when the image of each source point is not separated from the image of neighboring source points. This is because, in general, the light field from each source point is partially coherent with those from neighboring source points. However, if all the sources are completely incoherent with each other, then a complete de-convolution is possible even if the image of each source is overlapped with those of other sources. The emission areas 124 (See, e.g., FIG. 3B, FIG. 10) constitute fluorescent sources that are incoherent with each other. Therefore, a complete de-convolution is possible even when the corresponding image pixels 124' overlap.

Calibration

To accurately obtain the intensity of each image pixel 124' corresponding to each emission area 124, it is necessary to accurately determine both the position and the image profile of the image pixels. The position can be measured accurately via recording a snapshot of the interference-pattern image 200 and using the FFT technique to assess the null positions between the fringes that correspond to emission areas 124. This requires changing the filter 152 in front of the fluorescence camera 150 from one that specifically excludes the narrow-band inhibition wavelength $\lambda_2$ to one that specifically passes it. Tilting either filter 152 is best avoided since tilting a plate of finite thickness results in a lateral offset.

An alternate technique, and one that requires no filter change, is simply to place a coated calibration artifact 120A (FIG. 14) under the objective lens 100 and observe the fluorescence pattern. If the calibration artifact 120A is patterned in such a way that only every 3rd or 4th null position contains fluorescent material, then each image profile should be cleanly separated from its nearest neighbors' and then readily measured. Similarly, the position of each image can be measured. Neither the fringe spacing nor the image profile is likely to vary very much from one image to the next.

In an example method, the non-uniformity of the activation illumination combined with changes in the intensity of the inhibition pattern and the sensitivity variation over the detector elements DE is measured. The example method employs a technique similar to that described above, but with calibration artifact 120A having a uniform coating of fluorescent material. The variation in activation illumination and any changes in the intensity of the interference-fringe patterns 202X and 202Y should have a very low spatial-frequency content unless, for example, there is a dust particle present on calibration artifact 120A. The sharp discontinuity caused by a dust particle could be detected and removed by shifting the artifact and re-measuring. The sensitivity changes between detector elements DE are generally very small and vary randomly between the detector elements.

De-Convolution

There are two ways to account for the finite size of detector elements DE. One method is to de-convolve the image and the other is to convolve the PSF with the same detector element. The de-convolution of the image will be unstable and time-consuming. Therefore, convoluting the PSF with the same detector-element size may be preferred. The above equations are invariant as long as the detector-element size is the same or smaller than Nyquist size, which is defined by $\lambda/(4NA)$. That is, as long as the same detector-element size is applied to both image and PSF, the effect of a finite detector-element size is the same.

Thus, the above equations are valid as long as the same detector-element size is applied to both the image and the PSF. This invariance of the equations may not be understood easily in x-space (object or image-plane space), but can be understood easily in frequency space (i.e., Fourier-transform space or pupil space). In summary, our case is a special case that allows us to solve the problem of the finite detector-element size through the convolution of the PSF with the same detector-element size. The problem does not need to be solved through image de-convolution.

One assumption implicit in the equations set forth above is that the coordinate system of the PSF is the same as that of the image. This may not be true in practice, as there can be some unknown amount of sub-resolution mismatch between the two coordinate systems. In this case, we have to determine not only all the intensities of emission areas 124 but also, at the same time, the amount of coordinate mismatch. In this case, many interpolations of either the image or the PSF will be needed. Fortunately, the FFT-based interpolation will do the job fast and accurately.

Two-Photon Processes

Ideally, two-photon processes would be used to promote the excitation of electrons from the set of molecular vibrational levels that constitute the $S_0$ molecular ground state. This is better than using a single-photon process because the absorption coefficient of the material at the single-photon wavelength is typically quite high, allowing only the top layer to be excited. In contrast, the fluorescent material is usually quite transparent at a wavelength twice as long as the single-wavelength resonance, and this allows 3-dimensional probing of a thick object. This fact has been used advantageously in 3-dimensional imaging, where high numerical apertures are used to create high intensities in a small volume of resist to write a voxel, i.e., a 3-dimensional detector element. The downside is that high intensities are required and usually only one voxel can be written at a time, so the process is relatively slow. The resist films typically used in IC lithography are relatively thin, ~0.1 micron, and speed is critical, so for this application a single-photon process seems best.

Detection Wavelength

The dual-wavelength technique uses the green wavelength $\lambda_2$ to STimulate Emission-Depletion (STED) of excited electrons from the lowest vibrational state of the Si molecular orbital excited state. The wavelength used for inhibition, also called the STED wavelength, is chosen up-wavelength of the peak of the emission spectrum (i.e., is of lower energy) because a small part of this spectrum is typically overlapped with the absorbance band that gives rise to the Si-excited state in the first place.

To avoid any possibility that the wavelength chosen for inhibition could also cause activation, the inhibition wavelength $\lambda_2$ is usually up-wavelength of the peak emission wavelength. To gain the maximum signal to noise [ratio?], fluorescence should be detected across the entire emission band. It is important to completely exclude those wavelengths used to activate and to inhibit fluorescence emission since these intensities will typically be much stronger than the fluorescence intensity.

Image Scanning

In some applications, such as photo-mask or wafer inspection, it is desirable to carefully examine or inspect an object that is much larger than the instantaneous field of the objective lens or the detector 154. In such a case, it is desirable to scan the field of objective lens 100 back and forth across object 122 at a constant velocity while taking a series of pictures (i.e., capturing a series of images) so that each point on the substrate is contained in $n^2$ frames and each of the $n^2$ frames corresponds to a different fringe position. In this case, n is the ratio between the fringe spacing and the size of the emission area 124. The image blur normally associated with a moving object can be completely (or substantially) eliminated by locking the interference-pattern image 200 to the object 122 during the exposure of each frame and by including the image motion on the fluorescence camera photodetector 154 in the de-convolution algorithm.

Thus, in an example, scanning is used to continuously build up a high-resolution picture, which in some cases can be inspected continuously as it is obtained. Sometimes inspection simply requires a pixel-by-pixel comparison of the new picture with either a picture obtained previously or an ideal model. The very detailed image thus obtained can also be placed in a computer database, which is then examined using a program designed to find defects or specific patterns. The portion of the pattern containing the defects or the specific pattern defect can also be displayed to the operator.

Another method according to synchronizing the motion of interference-pattern image 200 with the motion of object 122 during the imaging process involves transferring the accumulated charge collected during the exposure from one row of detector elements DE to the next in synchrony with the image movement relative to detector plane DP. Doing so substantially eliminates image smear and allows the collection of many more photons from each fluorescent super-resolution area. The latter process is known as Time Delay Integration (TDI) scanning. This process is very efficient if the picture obtained contains all the information desired. In this case, improving the resolution by n-times requires the acquisition of $n^2$ snapshots. Using conventional TDI detectors would therefore require repeating each scan $n^2$ times.

The alternative to using a TDI detector and using $n^2$ scans is to scan more slowly using a large, two-dimensional photodetector 154, which captures $n^2$ snapshots as a point on object 122 is scanned across the photodetector. During the formation of a snapshot, i.e., while the photo-electrons are being integrated, the interference-pattern image 200 is synchronized with the movement of object 122.

Figure 14:
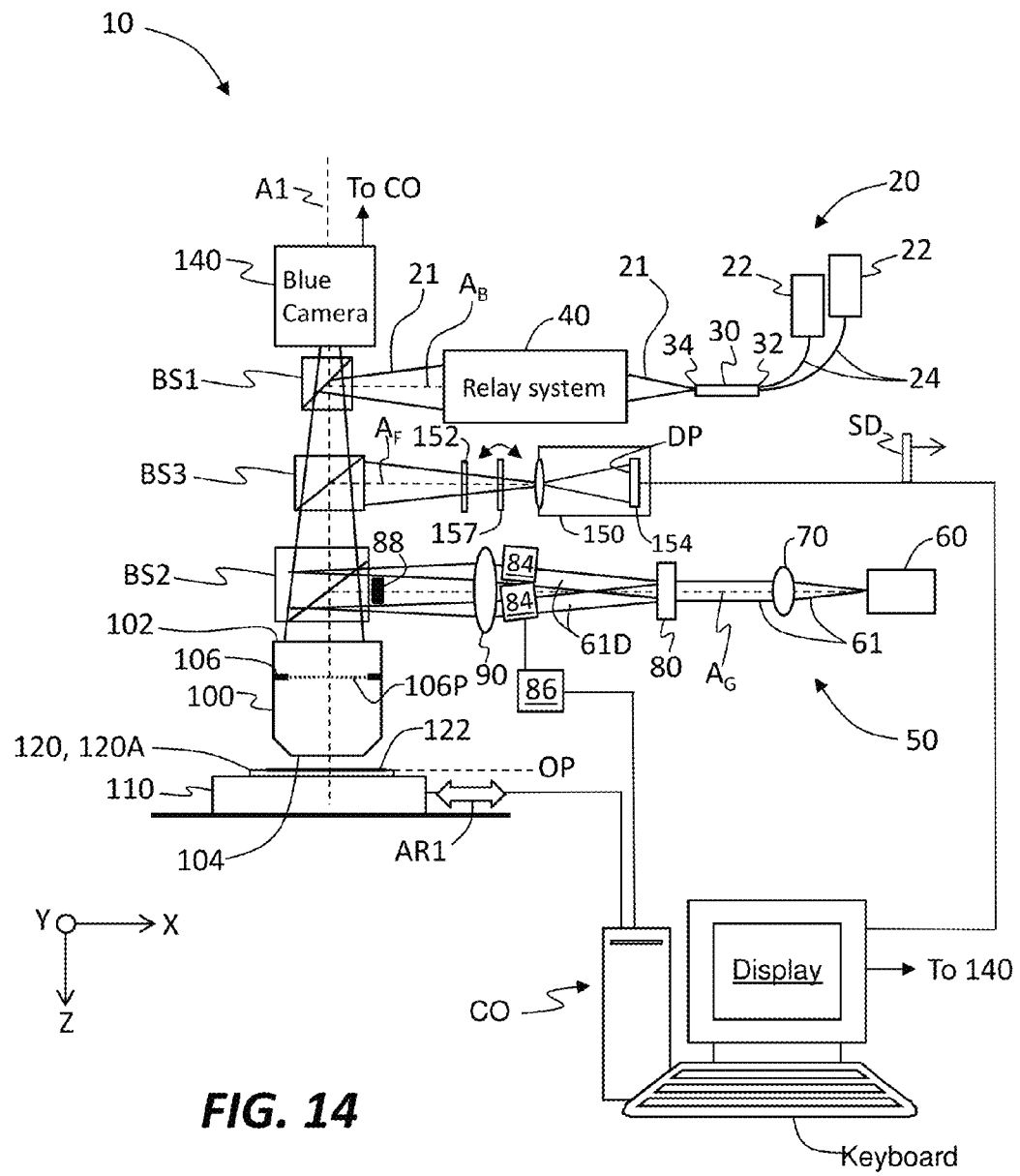
FIG. 14 is similar to FIG. 1 and illustrates an example embodiment of the microscope having a scanning configuration.

FIG. 14 is similar to FIG. 1 and illustrates an example microscope 10 configured for scanning. The scanning motion along the X-direction is illustrated by arrow AR1. The stage 110 is configured to scan in the X-Y plane and also to move in the Z-direction to assist with focus and alignment. In this example, image-motion compensation is provided by a rotating a tilt plate 157, which is located between fluorescence camera 150 and objective lens 100. The rotational velocity of tilt plate 157 is chosen so that the position of a point on the moving (scanned) object 122 is kept locked onto the same point of photodetector 154 during the exposure of a frame (i.e., the capture of an image). Each time a snapshot is taken, tilt plate 157 is re-adjusted to its starting point, and the interference-pattern image 200 is moved by one super-resolution element (i.e., one emission area 124) normal to the scan direction. Once synchronization is achieved between the rotation velocity of tilt plate 157 and the motion of object 122, another snapshot is taken.

After every n snapshots, the fringes running parallel to the scan direction are stepped a distance corresponding to the spacing between adjacent emission areas 124, so that after $n^2$ snapshots the entire object 122 has been super-resolution imaged onto photodetector 154. The $n^2$ snapshots can then be combined to produce a super-resolution image of the object area scanned across photodetector 154. An example of such a super-resolution image is shown in the example super-resolution image of FIG. 10C.

The main drawback to this technique is the time lost to re-setting the tilt plate 157. If acoustic modulators or a Pockels cell or a Kerr cell is used to move the fringes, then the response time is negligible compared to the time taken to re-set the tilt-plate 157. This is true even if the tilt plate 157 is mounted on a resonant scanner. An advantage of using an acoustic-modulator fringe [fringe→phase?] shifter is that the total amount of phase shift is unlimited. Acoustic modulators typically operate above 100 MHz, so a 5 MHz servo-bandwidth is possible. In comparison, a resonating tilt plate 157 might operate at several hundred hertz. Thus, if 100 snapshots are required and each cycle takes 5 ms, then scanning the length of photodetector 154 will take about 0.5 seconds.

To capture a blur-free super-resolution image of emission areas 124, the interference-fringe patterns 202X and 202Y need to be locked to object 122 during the exposure of a frame. However, as the above analysis has shown, it is not imperative to lock object 122 onto the fluorescence camera 150 during the exposure, since this smear is similar in nature to the overlap of the point spread functions on adjacent detector elements DE. Motion of the image on photodetector 154 increases the extent of the overlap in the scan direction. A super-resolution image can still be obtained by de-convolving this effect to yield an accurate estimate of the relative intensity of each super-resolution element 124.

Process Flow

The process flow for obtaining a super-resolution image of object 122 as described above in detail is summarized below using four main steps (I through VI), each step having a one or more sub-steps (1), (2), etc.

I. System Calibration (1) Using a uniformly coated calibration artifact 120A, measure the combined effects of the non-uniformity in the illumination of active light 21, small variations in the intensity of the interference-pattern image 200 across the field of objective lens 100, and sensitivity variations over photodetector 154 (e.g., detector element-to-detector element variations).

(2) Using a periodically patterned calibration artifact 120A having a uniform fluorescent coating, measure the PSF convolved with the emission profile of the object 122 as convolved with the finite size of the detector elements DE of photodetector 154. Define this PSF as $PSF_C$. The spacing between the periodic patterns of the calibration artifact 120A is chosen so that the PSFs between the nearest calibrated points do not overlap significantly. The $PSF_C$ is not expected to vary much across the field and, in an example embodiment of the method, can be considered constant across the field.

(3) Use the data obtained in step (1) to correct the data obtained in step (2) by dividing the intensity obtained from each detector element DE in (2) by the corresponding intensity from the same detector element DE in step (1).

(4) Using the FFT method described above and the data collected in step (2) above, calculate the positions of each fluorescence emission area 124 relative to photodetector 154 of fluorescence camera 150.

II. Obtain Raw Picture Data (1) Capture $n^2$ pictures from $n^2$ positions of interference-fringe patterns 202X and 202Y, where n is the ratio of the spacing of the fringe patterns to the width of emission areas

124. Typically, the fringe patterns are moved 1/n of a fringe space either in the X-direction or the Y-direction between the capturing of each picture.

III. Reduce Each Picture (1) Correct the intensity of each detector element DE in each picture using the data obtained in step I(1). This procedure would be identical to that employed in step I(3).

(2) Using the exact position of image pixels 124' on photodetector 154 as corrected for the shift in the fringe position, de-convolve the overlapping camera detector signals SD to obtain the intensity of each isolated fluorescence emission area 124. In this case, the de-convolution is done using a simple regression technique that uses the $PSF_C$ measurement obtained in step I(2) and that varies only slightly across the field. Each completed picture consists of a regular pattern of image pixels 124'.

IV. Produce a Super-Resolution Picture (1) Combine all the $n^2$ pictures containing sparse isolated pixels 124' into a super-resolution picture having a contiguous set of pixels.

It will be apparent to those skilled in the art that various modifications and variations can be made to the present disclosure without departing from the spirit and scope of the disclosure. Thus it is intended that the present disclosure cover the modifications and variations of this disclosure, provided they come within the scope of the appended claims and their equivalents.

What is claimed is:

1. A method according to forming a super-resolution image of an object that fluoresces at an activation wavelength and is inhibited from fluorescing at an inhibition wavelength, comprising:
   a) using light having the inhibition wavelength, sequentially forming $n^2$ interference-pattern images on the object to define fluorescence emission areas of the object, where n is an integer equal to 2 or greater;
   b) illuminating the object with light of the activation wavelength for each of the $n^2$ interference-pattern images to cause the fluorescence emission areas to emit fluorescent light at a fluorescent wavelength;
   c) capturing $n^2$ sparse object images that include images of the emission areas convolved with respective point spread functions (PSF), wherein the emission areas are smaller than the PSFs;
   d) for each of the sparse object images, de-convolving each of the emission-area images to obtain emission-area image intensities;
   e) combining the emission-area image intensities from the $n^2$ sparse object images to form the super-resolution image of the object; and
   further comprising performing a calibration that comprises at least one of:
   i) measuring and compensating for a distortion in the interference-pattern image; and ii) measuring and compensating for a non-uniformity of the activation-wavelength illumination.

2. The method according to claim 1, further comprising determining positions of the emission areas by capturing an image of one of the interference-pattern images and performing a Fourier analysis of the captured interference-pattern image.

3. The method according to claim 1, further including displaying the super-resolution image in a manner representative of the emission-area intensities.

4. The method according to claim 1, wherein the PSFs are determined as a function of their position at the object.

5. The method according to claim 1, wherein the object comprises a photoresist layer.

6. The method according to claim 1, wherein the interference-pattern image is formed by at least two pairs of diffracted light beams.

7. The method according to claim 1, wherein the $n^2$ interference-pattern images consist of crossed interference fringes, and where forming the different interference-pattern images includes shifting the interference fringes.

8. The method according to claim 1, wherein the captured $n^2$ sparse object images are stored in a computer-readable memory, and wherein instructions embodied in a computer-readable medium cause a computer to perform acts d) and e).

9. The method according to claim 1, wherein the light of the activating wavelength has a first intensity, the light of the inhibiting wavelength has a second intensity, and wherein the first and second intensities are selected to define a select size for the fluorescence emission areas.

10. The method according to claim 1, further including scanning the object relative to an objective lens and a photodetector while maintaining a substantially fixed position of the sparse object images at the photodetector.

11. The method according to claim 1, further including capturing with the photodetector at least one of: an image of the interference-pattern image and the activation-light illumination.

12. The method according to claim 1, further comprising capturing an image of the object at the first wavelength and inspecting the captured image to evaluate a characteristic of at least one of: i) one or more of the interference-pattern images and ii) the activation-light illumination.

13. The method according to claim 1, wherein each sparse object image is captured by a photodetector comprising an array of detector elements, each of which has a detector-element size, and further comprising reducing or eliminating a quantization effect caused by the array of detector elements by quantizing the PSFs to substantially match the detector-element size.

14. The method according to claim 1, further including performing calibration imaging using a calibration artifact in place of the object.

15. A microscope for forming a super-resolution image of an object that fluoresces at an activation wavelength and is inhibited from fluorescing at an inhibition wavelength, comprising:
   an objective lens arranged adjacent the object, the objective lens having a resolution and at least one point spread function (PSF);
   an interference pattern generator that operates cooperatively with the objective lens to generate an interference-pattern image on the object with first light of the inhibition wavelength, wherein the interference-pattern image comprises at least first and second sets of interference fringes;
   a light-source system that operates cooperatively with the objective lens to illuminate the object with second light having the activation wavelength, thereby defining on the object, in combination with the interference-pattern image, a plurality of sub-resolution fluorescence emission areas that emit fluorescent light, and wherein the image-pattern generator is adapted to shift at least one of the first and second sets of interference fringes relative to the object to shift a location of the fluorescence emission areas;

a fluorescence camera and filter that operate cooperatively with the objective lens to capture an image of the fluorescence emission areas and in response generate a photodetector signal; and a controller that receives the photodetector signal, the controller having instructions embodied in a computer-readable medium that cause the controller to perform a de-convolution of the captured image based on the at least one PSF to determine emission-area image intensities that define the super-resolution image.

16. The microscope according to claim 15, wherein the photodetector includes an array of detector elements, wherein the captured image includes image pixels defined by the images of the fluorescence emission areas, with each pixel covered by at least two detector elements.

17. The microscope according to claim 15, wherein the object is supported by a stage that is moveable relative to the objective lens.

18. The microscope according to claim 15, wherein the interference-pattern generator and light-source system are adapted to control respective first and second intensities of the first light and second light, wherein the first and second intensities define a size of the fluorescence emission areas.

19. The microscope according to claim 15, further including an inspection camera that operates cooperatively with the objective lens to capture images of the object at the first wavelength.

20. The microscope according to claim 15, further comprising means for synchronizing movement of the interference-pattern image with movement of the object.

\* \* \* \* \*